United States Patent
Dassel et al.

(10) Patent No.: US 6,294,689 B1
(45) Date of Patent: Sep. 25, 2001

(54) METHODS FOR REMOVING CATALYST AFTER OXIDATION OF HYDROCARBONS

(75) Inventors: Mark W. Dassel, Indianola; Ader M. Rostami, Bainbridge Island; David C. DeCoster, Buckley, all of WA (US); Eustathios Vassiliou, Newark, DE (US)

(73) Assignee: RPC Inc., Atlanta, GA (US)

( * ) Notice: Subject to any disclaimer, the term of this patent is extended or adjusted under 35 U.S.C. 154(b) by 0 days.

(21) Appl. No.: 09/665,501

(22) Filed: Sep. 19, 2000

Related U.S. Application Data

(63) Continuation of application No. 09/267,572, filed on Mar. 12, 1999, now Pat. No. 6,143,927, which is a continuation of application No. 08/931,035, filed on Sep. 16, 1997, now abandoned, which is a continuation-in-part of application No. 08/876,692, filed on Jun. 16, 1997, which is a continuation-in-part of application No. 08/824,992, filed on Mar. 27, 1997, now Pat. No. 5,922,908, and a continuation-in-part of application No. 08/812,847, filed on Mar. 6, 1997.

(60) Provisional application No. 60/020,798, filed on Jun. 24, 1996.

(51) Int. Cl.⁷ ............... C07C 51/412; C07C 45/78; C07C 409/02; C07C 37/70

(52) U.S. Cl. ............ 562/486; 562/593; 528/176; 528/288; 528/308; 528/322; 528/335; 568/357; 568/366; 568/558; 568/836

(58) Field of Search ................. 562/542, 543, 562/523, 486, 412, 593; 528/176, 288, 308, 322, 335; 568/357, 366, 558, 836

(56) References Cited

U.S. PATENT DOCUMENTS

| | | |
|---|---|---|
| 1,121,532 | 12/1914 | Newberry . |
| 2,014,044 | 9/1935 | Haswell .................... 75/17 |
| 2,223,493 | 12/1940 | Loder ..................... 260/537 |
| 2,223,494 | 12/1940 | Loder ..................... 260/586 |
| 2,301,240 | 11/1942 | Baumann et al. ............ 183/115 |
| 2,439,513 | 4/1948 | Hamblet et al. .............. 260/533 |
| 2,557,282 | 6/1951 | Hamblet et al. .............. 260/533 |
| 2,565,087 | 8/1951 | Porter et al. ............ 260/631 |
| 2,980,523 | 4/1961 | Dille et al. ................ 48/215 |
| 3,161,603 * | 12/1964 | Leyshon et al. ............. 252/413 |
| 3,231,608 | 1/1966 | Kollar ................... 260/533 |
| 3,234,271 | 2/1966 | Barker et al. ............. 260/531 |
| 3,290,369 | 12/1966 | Bonfield et al. ............ 260/537 |
| 3,361,806 | 1/1968 | Lidov ................... 260/531 |
| 3,515,751 | 6/1970 | Oberster et al. ............ 260/533 |
| 3,530,185 | 9/1970 | Pugi ..................... 260/586 |
| 3,613,333 | 10/1971 | Gardenier ................. 55/89 |
| 3,677,696 | 7/1972 | Bryk et al. ................. 23/2 |
| 3,839,435 | 10/1974 | Shigeyasu et al. ........... 260/524 R |
| 3,928,005 | 12/1975 | Laslo ..................... 55/73 |
| 3,932,513 | 1/1976 | Russell .................. 260/586 |
| 3,946,076 | 3/1976 | Paasen et al. ............. 260/586 |
| 3,957,876 | 5/1976 | Rapoport et al. ........... 260/586 |
| 3,987,100 | 10/1976 | Barnette et al. ........... 260/586 |
| 3,987,808 | 10/1976 | Carbonell et al. ........... 137/3 |
| 4,025,498 | 5/1977 | Buss et al. ............... 260/95 A |
| 4,039,304 | 8/1977 | Bechthold et al. ............ 55/10 |
| 4,055,600 | 10/1977 | Langley et al. ............. 260/586 |
| 4,065,527 | 12/1977 | Graber ................... 261/79 A |
| 4,308,037 | 12/1981 | Meissner et al. ............. 55/10 |
| 4,332,590 | 6/1982 | Smith ................... 23/230 A |
| 4,361,965 | 12/1982 | Goumondy et al. ........... 34/57 |
| 4,370,304 | 1/1983 | Hendriks et al. ............ 422/224 |
| 4,394,139 | 7/1983 | Board ................... 55/20 |
| 4,419,184 | 12/1983 | Backlund ................. 162/49 |
| 4,423,018 | 12/1983 | Lester, Jr. et al. ........... 423/243 |
| 5,061,453 | 10/1991 | Krippl et al. .............. 422/106 |
| 5,104,492 | 4/1992 | King et al. ............... 203/15 |
| 5,123,936 | 6/1992 | Stone et al. .............. 55/8 |
| 5,170,727 | 12/1992 | Nielsen ................... 110/346 |

(List continued on next page.)

FOREIGN PATENT DOCUMENTS

| | | |
|---|---|---|
| 4426132A1 | 1/1996 | (DE) . |
| 4427474 A1 | 2/1996 | (DE) . |
| 439 007 A2 | 7/1991 | (EP) . |
| 729 084 A1 | 8/1996 | (EP) . |
| 729 085 A1 | 8/1996 | (EP) . |
| 751 105 A2 | 1/1997 | (EP) . |
| 2 722 783 A1 | 1/1996 | (FR) . |
| 415172 | 8/1934 | (GB) . |
| 738808 | 10/1955 | (GB) . |
| 1143213 | 2/1969 | (GB) . |
| 2 014 473 A | 8/1979 | (GB) . |
| 864106 | 3/1991 | (GB) . |
| 96/03365 * | 2/1996 | (WO) . |
| WO96/03365 | 2/1996 | (WO) . |
| WO 96/40610 | 12/1996 | (WO) . |
| WO 97/49485 | 12/1997 | (WO) . |

OTHER PUBLICATIONS

E. Sorribes et al., "Formación de neuvas fases en el proceso de obtención de ácido adípico: causas y efectos que provocan," *Rev. R. Acad. Cienc. Exactas, Fis. Nat. Madrid* (1987), 81 (1), 233–5 (+ English language translation).

Primary Examiner—Rosalynd Keys
(74) Attorney, Agent, or Firm—Seed Intellectual Property Law Group PLLC

(57) ABSTRACT

This invention relates to oxidative methods for controlling the oxidation of a class of compounds, including hydrocarbons, such as cyclohexane for example, alcohols, such as cyclohexanol for example, ketones, such as cyclohexanone for example, and peroxides, such as cyclohexylhydroperoxide for example, to intermediate oxidation products, such as adipic acid for example, by the removing the catalyst, such as cobalt compounds for example, from the oxidation mixture, outside the oxidation zone, after the oxidation has taken place at least partially. The catalyst is at least partially precipitated by following the steps of changing the temperature to be within a specific range, and sequentially reducing the water level to such a degree that causes the catalyst to precipitate. The precipitated catalyst is thereafter preferably filtered from the oxidation mixture and recycled to the oxidation zone.

55 Claims, 11 Drawing Sheets

U.S. PATENT DOCUMENTS

| | | | |
|---|---|---|---|
| 5,221,800 * | 6/1993 | Park et al. | 562/543 |
| 5,244,603 | 9/1993 | Davis | 261/87 |
| 5,270,019 | 12/1993 | Melton et al. | 422/234 |
| 5,271,904 | 12/1993 | Esposito et al. | 422/105 |
| 5,286,458 | 2/1994 | Yang et al. | 422/168 |
| 5,294,378 | 3/1994 | Succi et al. | 261/130 |
| 5,312,567 | 5/1994 | Kozma et al. | 261/87 |
| 5,321,157 | 6/1994 | Kollar | 562/543 |
| 5,374,767 | 12/1994 | Drinkard et al. | 560/193 |
| 5,396,850 | 3/1995 | Conochie et al. | 110/346 |
| 5,399,750 | 3/1995 | Brun et al. | 562/553 |
| 5,463,119 | 10/1995 | Kollar | 562/543 |
| 5,502,245 | 3/1996 | Dassel et al. | 562/413 |
| 5,516,423 | 5/1996 | Conoby et al. | 210/85 |
| 5,558,842 | 9/1996 | Vassiliou et al. | 422/108 |
| 5,580,531 | 12/1996 | Vassiliou et al. | 422/108 |
| 5,654,475 | 8/1997 | Vassiliou et al. | 562/413 |
| 5,801,273 | 9/1998 | Vassiliou et al. | 562/413 |
| 5,801,282 | 9/1998 | Dassel et al. | 562/413 |
| 5,817,868 | 10/1998 | Rostami et al. | 562/413 |
| 5,824,819 | 10/1998 | Dassel et al. | 562/529 |
| 5,883,292 | 3/1999 | Dassel et al. | 562/413 |
| 5,908,589 | 6/1999 | DeCoster et al. | 264/37.18 |
| 5,922,908 | 7/1999 | DeCoster et al. | 562/543 |
| 5,929,277 | 7/1999 | DeCoster et al. | 562/593 |
| 6,037,491 | 3/2000 | Vassiliou et al. | 562/413 |
| 6,039,902 | 3/2000 | Rostami et al. | 264/37.18 |
| 6,103,933 | 8/2000 | DeCoster et al. | 562/509 |
| 6,129,875 | 10/2000 | Dassel et al. | 264/176.1 |

* cited by examiner

METHODS FOR REMOVING CATALYST AFTER OXIDATION OF HYDROCARBONS

CROSS-REFERENCES TO RELATED APPLICATIONS

This application is a continuation of U.S. application Ser. No. 09/267,572, filed Mar. 12, 1999 (now U.S. Pat. No. 6,143,927); which is a continuation of U.S. patent application Ser. No. 08/931,035, filed Sep. 16, 1997 (now abandoned), which is a continuation-in-part of U.S. patent application Ser. No. 08/876,692, filed Jun. 16, 1997, which is a continuation-in-part of allowed U.S. patent application Ser. No. 08/812,847, filed on Mar. 6, 1997, which in turn claims priority of Provisional Application No. 60/020,798, filed on Jun. 24, 1996; and is a continuation-in-part of U.S. patent application Ser. No. 08/824,992, filed Mar. 27, 1997 (now U.S. Pat. No. 5,922,908, issued Jul. 13, 1999); all of which are incorporated herein by reference.

FIELD OF THE INVENTION

This invention relates to methods of oxidizing hydrocarbons, such as cyclohexane for example, to respective intermediate oxidation products, such as adipic acid for example, and more specifically, how to remove catalyst after the reaction, preferably for recycling.

BACKGROUND OF THE INVENTION

There is a plethora of references (both patents and literature articles) dealing with the formation of acids, one of the most important being adipic acid, by oxidation of hydrocarbons. Adipic acid is used to produce Nylon 66 fibers and resins, polyesters, polyurethanes, and miscellaneous other compounds.

There are different processes of manufacturing adipic acid. The conventional process involves a first step of oxidizing cyclohexane with oxygen to a mixture of cyclohexanone and cyclohexanol (KA mixture), and then oxidation of the KA mixture with nitric acid to adipic acid. Other processes include, among others, the "Hydroperoxide Process," the "Boric Acid Process," and the "Direct Synthesis Process," which involves direct oxidation of cyclohexane to adipic acid with oxygen in the presence of solvents, catalysts, and promoters.

The Direct Synthesis Process has been given attention for a long time. However, to this date it has found little commercial success. One of the reasons is that although it looks very simple at first glance, it is extremely complex in reality. Due to this complexity, one can find strikingly conflicting results, comments, and views in different references.

It is well known that after a reaction has taken place according to the Direct Synthesis, a mixture of two liquid phases is present at ambient temperature, along with a solid phase mainly consisting of adipic acid. The two liquid phases have been called the "Polar Phase" and the "Non-Polar Phase". However, no attention has been paid so far to the importance of the two phases, except for separating the adipic acid from the "Polar Phase" and recycling these phases to the reactor partially or totally with or without further treatment.

It is also important to note that most studies on the Direct Synthesis have been conducted in a batch mode, literally or for all practical purposes.

As aforementioned, there is a plethora of references dealing with oxidation of organic compounds to produce acids, such as, for example, adipic acid and/or intermediate products, such as for example cyclohexanone, cyclohexanol, cyclohexylhydroperoxide, etc.

The following references, among others, may be considered as representative of oxidation processes relative to the preparation of diacids and other intermediate oxidation products.

U.S. Pat. No. 5,463,119 (Kollar) discloses a process for the oxidative preparation of C5–C8 aliphatic dibasic acids by (1) reacting,
   (a) at least one saturated cycloaliphatic hydrocarbon having from 5 to 8 ring carbon atoms in the liquid phase and
   (b) an excess of oxygen gas or an oxygen-containing gas in the presence of
   (c) a solvent comprising an organic acid containing only primary and/or secondary hydrogen atoms and
   (d) at least about 0.002 mole per 1000 grams of reaction mixture of a polyvalent heavy metal catalyst;
(2) removing the aliphatic dibasic acid; and
(3) recycling intermediates, post oxidation components, and derivatives thereof remaining after removal of the aliphatic dibasic acid into the oxidation reaction.

U.S. Pat. No. 5,374,767 (Drinkard et al.) discloses formation of cyclohexyladipates in a staged reactor, e.g., a reactive distillation column. A mixture containing a major amount of benzene and a minor amount of cyclohexene is fed to the lower portion of the reaction zone and adipic acid is fed to the upper portion of the reaction zone, cyclohexyladipates are formed and removed from the lower portion of the reaction zone and benzene is removed from the upper portion of the reaction zone. The reaction zone also contains an acid catalyst.

U.S. Pat. No. 5,321,157 (Kollar) discloses a process for the preparation of C5–C8 aliphatic dibasic acids through oxidation of corresponding saturated cycloaliphatic hydrocarbons by (1) reacting, at a cycloaliphatic hydrocarbon conversion level of between about 7% and about 30%,
   (a) at least one saturated cycloaliphatic hydrocarbon having from 5 to 8 ring carbon atoms in the liquid phase and
   (b) an excess of oxygen gas or an oxygen containing gas mixture in the presence of
   (c) less than 1.5 moles of a solvent per mole of cycloaliphatic hydrocarbon (a), wherein said solvent comprises an organic acid containing only primary and/or secondary hydrogen atoms and
   (d) at least about 0.002 mole per 1000 grams of reaction mixture of a polyvalent heavy metal catalyst; and
(2) isolating the C5–C8 aliphatic dibasic acid. U.S. Pat. No. 3,987,100 (Barnette et al.) describes a process of oxidizing cyclohexane to produce cyclohexanone and cyclohexanol, said process comprising contacting a stream of liquid cyclohexane with oxygen in each of at least three successive oxidation stages by introducing into each stage a mixture of gases comprising molecular oxygen and an inert gas.

U.S. Pat. No. 3,957,876 (Rapoport et al.) describes a process for the preparation of cyclohexyl hydroperoxide substantially free of other peroxides by oxidation of cyclohexane containing a cyclohexane soluble cobalt salt in a zoned oxidation process in which an oxygen containing gas is fed to each zone in the oxidation section in an amount in excess of that which will react under the conditions of that zone.

U.S. Pat. No. 3,932,513 (Russell) discloses the oxidation of cyclohexane with molecular oxygen in a series of reaction zones, with vaporization of cyclohexane from the last reactor effluent and parallel distribution of this cyclohexane vapor among the series of reaction zones.

U.S. Pat. No. 3,530,185 (Pugi) discloses a process for manufacturing precursors of adipic acid by oxidation with an oxygen-containing inert gas which process is conducted in at least three successive oxidation stages by passing a stream of liquid cyclohexane maintained at a temperature in the range of 140° to 200° C. and a pressure in the range of 50 to 350 p.s.i.g. through each successive oxidation stage and by introducing a mixture of gases containing oxygen in each oxidation stage in an amount such that substantially all of the oxygen introduced into each stage is consumed in that stage thereafter causing the residual inert gases to pass counter-current into the stream of liquid during the passage of the stream through said stages.

U.S. Pat. No. 3,515,751 (Oberster et al.) discloses a process for the production of epsilon-hydroxycaproic acid in which cyclohexane is oxidized by liquid phase air oxidation in the presence of a catalytic amount of a lower aliphatic carboxylic acid and a catalytic amount of a peroxide under certain reaction conditions so that most of the oxidation products are found in a second, heavy liquid layer, and are directed to the production of epsilon-hydroxycaproic acid.

U.S. Pat. No. 3,361,806 (Lidov et al.) discloses a process for the production of adipic acid by the further oxidation of the products of oxidation of cyclohexane after separation of cyclohexane from the oxidation mixture, and more particularly to stage wise oxidation of the cyclohexane to give high yields of adipic acid precursors and also to provide a low enough concentration of oxygen in the vent gas so that the latter is not a combustible mixture.

U.S. Pat. No. 3,234,271 (Barker et al.) discloses a process for the production of adipic acid by the two-step oxidation of cyclohexane with oxygen. In a preferred embodiment, mixtures comprising cyclohexanone and cyclohexanol are oxidized. In another embodiment, the process involves the production of adipic acid from cyclohexane by oxidation thereof, separation of cyclohexane from the oxidation mixture and recycle thereof, and further oxidation of the other products of oxidation.

U.S. Pat. No. 3,231,608 (Kollar) discloses a process for the preparation of aliphatic dibasic acids from saturated cyclic hydrocarbons having from 4 to 8 cyclic carbon atoms per molecule in the presence of a solvent which comprises an aliphatic monobasic acid which contains only primary and secondary hydrogen atoms and a catalyst comprising a cobalt salt of an organic acid, and in which process the molar ratio of said solvent to said saturated cyclic hydrocarbon is between 1.5:1 and 7:1, and in which process the molar ratio of said catalyst to said saturated cyclic hydrocarbon is at least 5 millimoles per mole.

U.S. Pat. No. 3,161,603 (Leyshon et al.) discloses a process for recovering the copper-vanadium catalyst from the waste liquors obtained in the manufacture of adipic acid by the nitric acid oxidation of cyclohexanol and/or cyclohexanone.

U.S. Pat. No. 2,565,087 (Porter et al.) discloses the oxidation of cycloaliphatic hydrocarbons in the liquid phase with a gas containing molecular oxygen and in the presence of about 10% water to produce two phases and avoid formation of esters.

U.S. Pat. No. 2,557,282 (Hamblet et al.) discloses production of adipic acid and related aliphatic dibasic acids; more particularly to the production of adipic acid by the direct oxidation of cyclohexane.

U.S. Pat. No. 2,439,513 (Hamblet et al.) discloses the production of adipic acid and related aliphatic dibasic acids and more particularly to the production of adipic acid by the oxidation of cyclohexane.

U.S. Pat. No. 2,223,494 (Loder et al.) discloses the oxidation of cyclic saturated hydrocarbons and more particularly to the production of cyclic alcohols and cyclic ketones by oxidation of cyclic saturated hydrocarbons with an oxygen-containing gas.

U.S. Pat. No. 2,223,493 (Loder et al.) discloses the production of aliphatic dibasic acids and more particularly to the production of aliphatic dibasic acids by oxidation of cyclic saturated hydrocarbons with an oxygen-containing gas.

German Pat. No. DE 44 26 132 A1 (Kysela et al.) discloses a method of dehydration of process acetic acid from liquid-phase oxidation of cyclohexane with air, in the presence of cobalt salts as a catalyst after separation of the adipic acid after filtration, while simultaneously avoiding cobalt salt precipitates in the dehydration column, characterized in that the acetic acid phase to be returned to the beginning of the process is subjected to azeotropic distillation by the use of added cyclohexane, under distillative removal of the water down to a residual content of less than [sic] 0.3–0.7%.

PCT International Publication WO 96/03365 (Constantini et al.) discloses a process for recycling a cobalt-containing catalyst in a direct reaction of oxidation of cyclohexane into adipic acid, characterized by including a step in which the reaction mixture obtained by oxidation into adipic acid is treated by extraction of at least a portion of the glutaric acid and the succinic acid formed during the reaction.

The patent literature is inconsistent and at least confusing regarding addition or removal of water in oxidations. For example:

U.S. Pat. No. 5,221,800 (Park et al.) discloses a process for the manufacture of adipic acid. In this process, cyclohexane is oxidized in an aliphatic monobasic acid solvent in the presence of a soluble cobalt salt wherein water is continuously or intermittently added to the reaction system after the initiation of oxidation of cyclohexane as indicated by a suitable means of detection, and wherein the reaction is conducted at a temperature of about 50° C. to about 150° C. at an oxygen partial pressure of about 50 to 420 pounds per square inch absolute.

U.S. Pat. No. 4,263,453 (Schultz et al.) discloses a process claiming improved yields by the addition of water at the beginning of the reaction, generally of the order of 0.5 to 15% relative to monobasic aliphatic acid solvent, and preferably 1 to 10% relative to the solvent.

U.S. Pat. No. 3,390,174 (Schultz et al.) discloses a process claiming improved yields of aliphatic dibasic acids when oxidizing the respective cyclic hydrocarbons at temperatures between 130° and 160° C., while removing the water of reaction substantially as quickly as it is formed.

None of the above references, or any other references known to the inventors disclose, suggest or imply, singly or in combination, control of oxidation reactions by adjusting the water level subject to the intricate and critical controls and requirements of the instant invention as described and claimed.

Our U.S. Pat. Nos. 5,580,531, 5,558,842, 5,502,245, and our co-pending applications Ser. No. 08/477,195 (filed Jun. 7, 1995), Ser. No. 08/587,967 (filed Jan. 17, 1996), and Ser. No. 08/620,974 (filed Mar. 25, 1996), all of which are incorporated herein by reference, describe methods and apparatuses relative to controlling reactions in atomized liquids. Our application Ser. No. 08/812,847, filed on Mar. 6, 1997, and our application Ser. No. 08/824,992, filed on Mar. 27, 1997 are both also incorporated herein by reference.

All of the following patent applications, which were filed simultaneously on May 21, 1997, are also incorporated herein by reference:

Now U.S. Pat. No. 5,801,273 of Eustathios Vassiliou, Mark W. Dassel, David C. DeCoster, Ader M. Rostami, and Sharon M. Aldrich, titled "Methods and Devices for Controlling the Reaction Rate of a Hydrocarbon to an Intermediate Oxidation Product by Pressure Drop Adjustments;"

U.S. Application Ser. No. 08/861,281 of Mark W. Dassel, Eustathios Vassiliou, David C. DeCoster, Ader M. Rostami, and Sharon M. Aldrich, titled "Methods for Controlling the Reaction Rate of a Hydrocarbon to an Intermediate Oxidation Product by Monitoring Flow of Incoming and Outcoming Gases;"

U.S. Application Ser. No. 08/861,180 of David C. DeCoster, Ader M. Rostami, Mark W. Dassel, and Eustathios Vassiliou, titled "Methods for Controlling the Oxidation Rate of a Hydrocarbon by Adjusting the Ratio of the Hydrocarbon to a Rate-Modulator;"

Now U.S. Pat. No. 5,824,819 of Mark W. Dassel, Eustathios Vassiliou, David C. DeCoster, and Ader M. Rostami, titled "Methods of Preparing an Intermediate Oxidation Product from a Hydrocarbon by Utilizing an Activated Initiator";

Now U.S. Pat. No. 5,817,868 of Ader M. Rostami, Mark W. Dassel, Eustathios Vassiliou, David C. DeCoster, titled "Methods and Devices for Controlling the Oxidation of a Hydrocarbon to an Acid by Regulating Temperature/Conversion Relationship in Multi-Stage Arrangements;"and U.S. Application Ser. No. 08/861,210 (now abandoned) of Eustathios Vassiliou, Ader M. Rostami, David C. DeCoster, and Mark W. Dassel, titled "Pseudo-Plug-Flow Reactor."

Further, our patent application Ser. No. 08/876,692, filed on Jun. 16, 1997, of Ader M. Rostami, David C. DeCoster, Eustathios Vassiliou, Mark W. Dassel, and Sharon M. Aldrich, titled "Devices for Detecting Formation of a Second Liquid Phase"is also incorporated herein by reference.

Our PCT patent application No. PCT/US97/10830, Publication No. WO 97/49485, filed on Jun. 23, 1996 of Mark W. Dassel, David C. DeCoster, Ader M. Rostami, Eustathios Vassiliou, and Sharon M. Aldrich, titled "Methods and Devices for Oxidizing a Hydrocarbon to Form an Acid" is incorporated herein by reference.

Also, our PCT patent application No. PCT/US97/12944, Publication No. WO 98/07677, filed on Jun. 23, 1996, of David C. DeCoster, Eustathios Vassiliou, Mark W. Dassel, Sharon M. Aldrich, and Ader M. Rostami, titled "Methods and Devices for Controlling the Reaction Rate and/or Reactivity of Hydrocarbon to an Intermediate Oxidation Product by Adjusting the Oxidant Consumption Rate" is incorporated herein by reference.

In addition, our patent application now U.S. Pat. No. 6,037,491, filed on Jun. 25, 1997, of Eustathios Vassiliou, Mark W. Dassel, Sharon M. Aldrich, Ader M. Rostami, and David C. DeCoster, titled "Methods and Devices for Controlling Hydrocarbon Oxidations to Respective Acids by Adjusting the Solvent to Hydrocarbon Ratio" is also incorporated herein by reference.

SUMMARY OF THE INVENTION

As aforementioned, this invention relates to methods of oxidizing hydrocarbons, such as cyclohexane for example, to respective intermediate oxidation products, such as adipic acid for example, and more specifically, how to remove catalyst after the reaction, preferably for recycling. More particularly, this invention pertains to a method of removing catalyst from a mixture comprising the catalyst and water, the mixture having been formed after reaction of a hydrocarbon with an oxidant to form an intermediate oxidation product at an operation temperature, in the presence of the catalyst, and water at a first water level, the method being characterized by the steps of:

(a) changing the operation temperature to a temperature at or above a precipitation temperature, at which and over which precipitation temperature, the catalyst in the mixture would precipitate, at least partially, if the water level in the mixture had been reduced to or under a precipitation water level;

(b) removing an adequate amount of water from the mixture, in order to bring the water level to or under the precipitation water level, thereby causing the catalyst to precipitate, at least partially; and (c) removing the precipitated catalyst from the rest of the mixture.

This invention is also related to a method of removing catalyst from a mixture comprising the catalyst and water, the mixture having been formed after reaction of a hydrocarbon with an oxidant to form an intermediate oxidation product at an operation temperature, in the presence of the catalyst, and water at a water level, the method being characterized by the steps of:

(d) changing the operation temperature to a temperature below a precipitation temperature, at which and over which precipitation temperature, the catalyst in the mixture would precipitate, at least partially, if the water level in the mixture had been reduced to or under a precipitation water level;

(e) removing an adequate amount of water from the mixture, in order to bring the water level to or under the precipitation water level, without causing the catalyst to precipitate;

(f) changing the temperature of step (d) to a temperature at or above the precipitation temperature, thereby causing the catalyst to precipitate at least partially; and (g) removing the precipitated catalyst from the rest of the mixture.

In the methods just described, and in other methods of the invention disclosed herein, unless otherwise stated, the order in which the steps are performed need not be the same order in which the steps are delineated. In other words, the methods of the present invention encompass methods wherein steps are performed in a sequence other than the listed sequence. Furthermore, the steps of the inventive method need not be performed sequentially. In other words, additional steps may be performed intermediate any two listed steps, and the resulting method is still encompassed by the claimed invention.

It is preferable that substantially all the water, which influences the catalyst precipitation process, is removed. Water bound in a manner that does not promote or hinder catalyst precipitation at a desired temperature is evidently immaterial as far as the catalyst precipitation process at the desired temperature is concerned.

The methods may further comprise a step of removing at least partially the intermediate oxidation product, preferably by centrifuging, filtering, or a combination thereof, either before or after at least partial removal of the catalyst.

The methods may comprise a step of forming a precipitate containing both precipitated intermediate oxidation product and catalyst, and a step of dissolving the precipitated catalyst in water.

According to the methods of the present invention, the water may also be removed in at least two stages, a first stage at which most of a desired amount of water is removed, and a second stage at which the rest of the desired amount of water is removed. This is particularly beneficial when the water level is reduced in a distillation column to just above the level at or under which catalyst precipitates, and the rest of the desired water is removed in a precipitation chamber. For example, the water in the second stage may be removed by stripping or forming an azeotrope with the hydrocarbon, or it may be removed by addition of an acid anhydride, which is preferably acetic acid anhydride, or it may be removed by distillation with simultaneous concentration of the mixture containing the catalyst and the water. Of course, the water in any stage may be removed by addition of an acid anhydride, which is preferably acetic acid anhydride.

Deposition of catalyst on solid surfaces may be reduced, and/or catalyst precipitation may be assisted by use of seeds added to the mixture. The seeds may comprise precipitated catalyst, from a step of the process.

The catalyst precipitation may also be conducted in at least two stages. For example, the catalyst may be precipitated partially in a distillation column, and partially in a precipitation/de-watering chamber.

The methods of this invention are particularly applicable in the case that:

the hydrocarbon comprises a compound selected from a group consisting of cyclohexane, cyclohexanone, cyclohexanol, cyclohexylhydroperoxide, o-xylene, m-xylene, p-xylene, a mixture of at least two of cyclohexane, cyclohexanone, cyclohexanol, cyclohexylhydroperoxide, and a mixture of at least two of o-xylene, m-xylene, p-xylene;

the oxidant comprises oxygen; and a major portion of the intermediate oxidation product comprises a compound selected from a group consisting of adipic acid, cyclohexanol, cyclohexanone, cyclohexylhydroperoxide, phthalic acid, isophthalic acid, terephthalic acid, a mixture of at least two of adipic acid, cyclohexanone, cyclohexanol, and cyclohexylhydroperoxide, and a mixture of at least two of phthalic acid, isophthalic acid, and terephthalic acid.

The catalyst may comprise a metal compound, which is preferably selected from a group consisting of Cu, Ag, Au, Mg, Ca, Sr, Ba, Zn, Cd, Hg, Al, Sc, Y, Ga, In, Tl, Ti, Zr, Hf, Ge, Sn, Pb, V, Nb, Ta, Cr, Mo, W, Mn, Tc, Re, Fe, Ru, Os, Co, Rh, Ir, Ni, Pd, Pt, and a combination thereof.

This invention is even more particularly applicable, in the case that the intermediate oxidation product comprises adipic acid, the hydrocarbon comprises cyclohexane, the catalyst comprises a cobalt compound, the gaseous oxidant comprises oxygen, and the mixture comprises acetic acid.

Further, the instant invention pertains to a method, wherein the intermediate oxidation product comprises a compound selected from a group consisting of adipic acid, phthalic acid, isophthalic acid, and terephthalic acid, and the method further comprises a step of reacting said intermediate oxidation product with a third reactant selected from a group consisting of a polyol, a polyamine, and a polyamide in a manner to form a polymer of a polyester, or a polyamide, or a (polyimide and/or polyamideimide), respectively. The method may further comprise a step of spinning the polymer into fibers.

The present invention also pertains to a reactor device for conducting an oxidation of a hydrocarbon to an intermediate oxidation product in the presence of a catalyst in a reaction mixture, and for separating at least part of the catalyst from the reaction mixture, the reactor device characterized by:

a reaction chamber for conducting the oxidation; and a catalyst removal assembly connected to the reaction chamber, the catalyst removal assembly comprising at least one of de-watering means for removing water from the reaction mixture, and thermal treatment means for thermally treating the reaction mixture, in a manner that catalyst precipitates.

The de-watering means preferably comprise a de-watering chamber, and a distillation column connected to the de-watering chamber. Preferably, a condenser is connected to the distillation column and a decanter is connected to the condenser.

The thermal treatment means may comprise one or more heat exchangers, and/or a thermal precipitation chamber.

The thermal precipitation chamber and the de-watering chamber may constitute a single chamber.

The reactor device of the instant invention may further comprise intermediate oxidation product removal means connected to the catalyst removal means, for removing intermediate oxidation product from the reaction mixture.

The intermediate oxidation product removal means may be disposed after the catalyst removal assembly and away from the reaction chamber, or they may be disposed between the catalyst removal assembly and the reaction chamber.

The reactor device may further comprise a water-wash station for removing catalyst from the intermediate oxidation product.

The de-watering means may comprise:

a distillation column having a stripper zone and a rectifier zone;

a re-boiler connected to the stripper zone; and a de-watering chamber connected to the distillation column.

The reactor device may further comprise means for causing precipitation of catalyst in the de-watering chamber, and/or means for causing precipitation of catalyst in the distillation column, and/or means for causing precipitation of catalyst partially in the distillation column and partially in the de-watering chamber.

The reactor device may further comprise a first solids separator for separating precipitated catalyst, and for producing a liquid free of precipitated catalyst. Part of the liquid, which is free of precipitated catalyst, may be re-cycled to the stripper zone of the distillation column, through the re-boiler.

Also, the reactor device may further comprise means for introducing seeds in one or both of the distillation column and the de-watering chamber. The seeds may comprise catalyst crystals originating from the precipitated catalyst.

Cooling at one or more stages may be performed by condensation or other cooling means, such as cooling coils for example, or both.

By the term "steady state" it is meant that the reaction has reached an equilibrium, which equilibrium, however, may be adjusted periodically or continuously in order to achieve a desired result. If for example more water is needed in the reaction zone to avoid catalyst precipitation, the water feed rate to the reaction zone may be increased appropriately, and still the reaction may be considered to be at a "steady state". Similarly, if less water is needed to avoid formation of two phases, the water feed rate to the reaction zone may be decreased appropriately, and still the reaction may be considered to be at a "steady state."

The terms "substantially single-phase liquid" and "substantially single liquid phase" are for all practical purposes synonymous for the purposes of this invention. They both intend to indicate that there is no second liquid phase present, while a solid phase may or may not be present. The terms "second phase formation" or "formation of a second phase" refer to a second liquid phase, and not to a solid phase, unless otherwise specified.

The term "level" of an ingredient (reactant, reaction product, intermediate oxidation product, inert matter, or any other type of matter present) includes both "relative level" and "percentage level". According to the instant invention, both methods and devices may perform by using either one or the other type of "levels". In some occasions it may be easier to use one type rather than the other. "Relative level" of an ingredient denotes the amount of the ingredient present in weight units or in volume units, in a reaction zone or in a cell for example, as compared to 100 units, in weight units or in volume units, respectively, of the rest of the ingredients present, or the rest of the ingredients under consideration. The rest of the ingredients present or the rest of the ingredients under consideration, in this case, have a constant ratio with respect to each other. On the other hand, "percentage level" is the level expressed as a percentage based on total amount of all or of a desired number of specific ingredients. The percentages may be expressed also either by weight or by volume.

Removal of water from a mixture includes binding the water in a manner that it is not free to act as water for the purposes of this invention. For example, reaction of an anhydride, such as acetic anhydride for example, with water contained in a mixture, is considered as water removal from the mixture, despite the fact the oxygen and hydrogen atoms, which constituted the reacted water molecule, are still present in the mixture.

All ratios and percentages are expressed by weight unless otherwise specified.

A controller, preferably a computerized controller, may handle with ease and accuracy either type of "level." Programming a computerized controller to perform such functions is a routine process, well known to the art. According to this invention, a controller, based on information received, from a reaction zone for example, controls feed rates, temperatures, pressures, and other parameters in order to achieve the desirable results. The controller may also be programmed, by techniques well known to the art, to include flow sheet simulation, which may account for vapor/liquid equilibrium and energy balance effects.

As aforementioned, these methods and devices are particularly suited in case that the hydrocarbon comprises cyclohexane, the mixture comprises acetic acid, and the catalyst comprises a cobalt salt.

BRIEF DESCRIPTION OF THE DRAWING

The reader's understanding of this invention will be enhanced by reference to the following detailed description taken in combination with the drawing figure, wherein.

DETAILED DESCRIPTION OF THE INVENTION

As aforementioned, this invention relates to methods and devices for oxidizing hydrocarbons, such as cyclohexane for example, to respective intermediate oxidation products, such as adipic acid for example, and more specifically, how to remove catalyst after the reaction, preferably for recycling.

Proper catalyst handling in oxidation reactions has always been a considerable problem in the art. According to the present invention, catalyst is precipitated at least partially from the reaction mixture after an oxidation has taken place by de-watering and/or thermal treatment. This presents enormous advantages, because the precipitated catalyst may be easily and efficiently recycled for repeated utilization. De-watering is preferably conducted by use of distillation columns and/or addition of anhydrides, preferably acetic acid anhydride. However, other methods, such as for example use of other de-watering compounds, are not excluded and may be used very effectively, especially in combination with distillation columns. Examples of other de-watering compounds are colloidal silica, calcium oxide, molecular sieves, etc.

It was found by the inventors that very important factors regarding catalyst precipitation are water level, catalyst level, hydrocarbon level, and temperature, among others, which include reaction products and by-products. For a given set of factors, catalyst precipitation is facilitated as the water level decreases, the catalyst level increases, the hydrocarbon level increases, and as temperature increases.

For better clarification of this invention, the examples given below assume that the hydrocarbon is cyclohexane, the intermediate oxidation product comprises adipic acid, the mixture contains a solvent comprising acetic acid, and the catalyst comprises a cobalt compound. It should be understood, however, that the teachings of this invention are applicable to different hydrocarbons, intermediate oxidation products, solvents, and catalysts than the ones used in the examples. Only minor modifications may be needed to fit each individual case.

Figure 1:
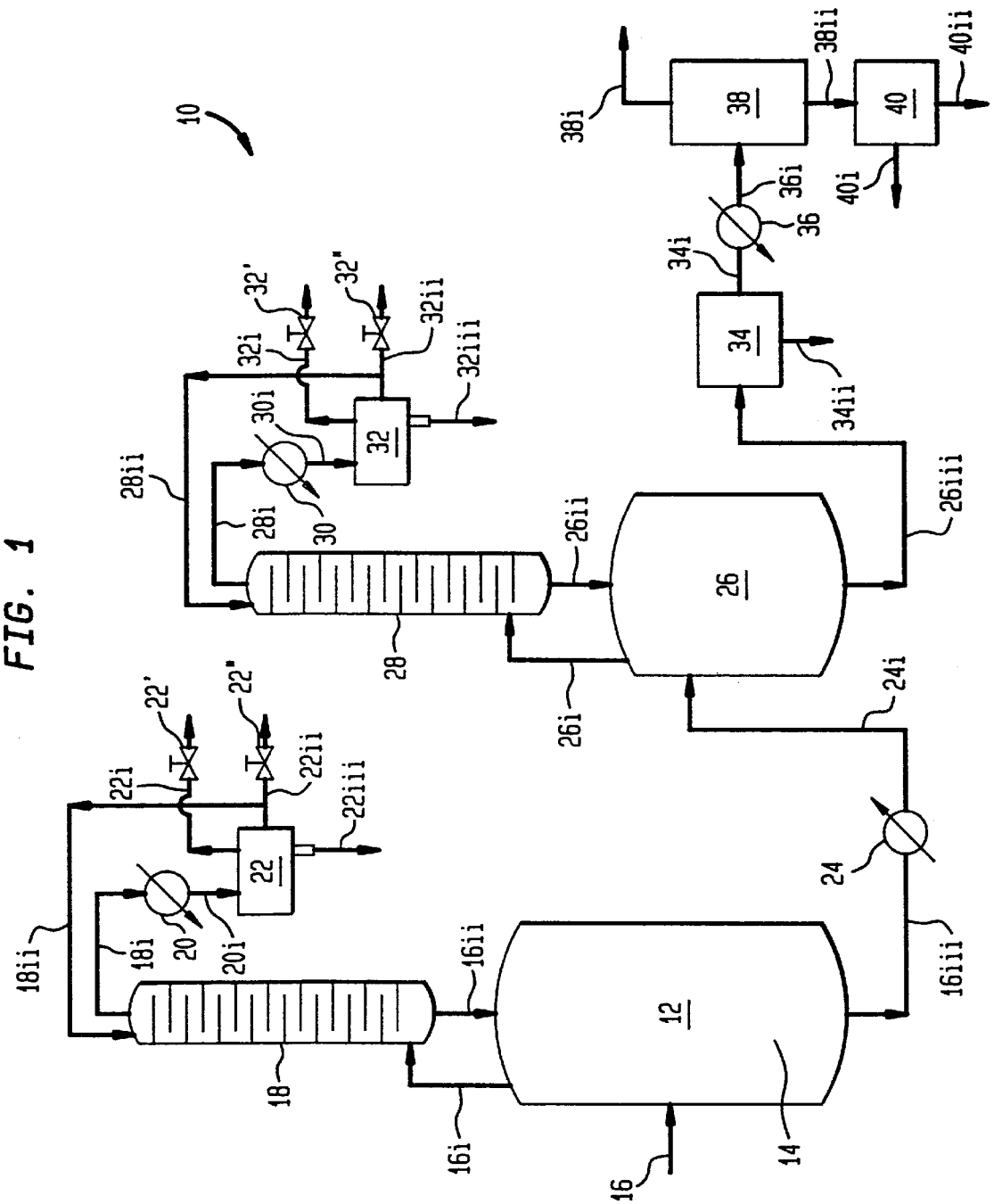
FIG. 1 illustrates a block diagram of a preferred embodiment of the present invention, wherein the thermal precipitation chamber and the de-watering chamber constitute a single chamber.

Referring now to FIG. 1, there is depicted a reactor system or device 10, comprising a reaction chamber 12 containing a reaction zone 14. The reactor system or device 10 is only partially shown for demonstrating the components necessary to exemplify the present invention. Miscellaneous treatment, product or by-product separation, recycling, etc. devices, well known to the art, are not shown for purposes of clarity and brevity.

Feeding means (for raw materials, miscellaneous recycled matter, gaseous oxidant, etc.) connected to the reaction chamber 12 are represented by a single feeding line 16 for purposes of clarity and brevity. However, it should be understood that, in practice, a number of individual lines may be used, including if appropriate, devices such as for example mixing vessels, heaters, coolers, etc.

Preferably a first distillation column 18 may also be utilized. The first distillation column 18 is connected at one end to the reaction chamber 12 through lines 16i and 16ii, while at the other end is connected to a first condenser 20 through line 18i. The first condenser 20 is in turn connected to a first decanter 22 through line 20i. The first decanter 22 has a first vent line 22i, a first cyclohexane (or other hydrocarbon) removal line 22ii, and a first water removal line 22iii. Lines 22i and 22ii are connected to valves 22' and 22", respectively. Line 22ii is also connected to line 18ii for recycling cyclohexane to the first distillation column 18.

The reaction chamber 12 is also connected to optional heater 24 through line 16iii. The optional heater 24 is in turn connected to the de-watering chamber 26.

A second distillation column 28 is connected at one end to the de-watering chamber 26 through lines 26I and 26ii, while at the other end is connected to a second condenser 30 through line 28i. The second condenser 30 is in turn connected to a second decanter 32 through line 30i. The second decanter 32 has a second vent line 32i, a second cyclohexane (or other hydrocarbon) removal line 32ii, and a second water removal line 32iii. Lines 32i and 32ii are connected to valves 32' (vent valve) and 32" (hydrocarbon sampling or removal valve), respectively. Line 32ii is also connected to line 28ii for recycling cyclohexane to the second distillation column 28.

The de-watering chamber 26 is also connected to a first solids separator 34 through line 26iii. The first solids separator 34 may be a filter, a centrifugal separator, or any other type of separator capable of separating solid from liquid matter. A line 34ii is connected to the first solids separator 34 for removing solid matter from said first solids separator. The first solids separator is also connected through line 34i to an optional cooler 36, which in turn is connected to a crystallizer 38 through line 36i. The crystallizer 38 is preferably a flash crystallizer, and it uses a pressure reduction line 38i. The pressure reduction (which may go from the operation pressure to any lower pressure, including sub-atmospheric, but preferably atmospheric) in the crystallizer 38, has as a result a substantially instantaneous drop in temperature, which in turn causes solids (such as adipic acid for example) to crystallize and precipitate. The crystallizer 38 is connected to a second solids separator 40 through line 38ii. The crystallized solids are separated and removed from the crystallizer through line 40ii, while the remaining liquids are removed from line 40i, for further treatment and/or recycling.

In operation of this embodiment, miscellaneous raw materials and recyclables, including in this example cyclohexane, acetic acid, cobalt compound catalyst, optional initiator (preferably cyclohexanone or acetaldehyde, or a mixture thereof), preferably water, and a gaseous oxidant, preferably comprising oxygen, enter the reaction zone 14, inside the reaction chamber 12, through the feeding means represented by line 16.

The oxidation is preferably brought to a steady state, and preferably the majority or all the heat of reaction is removed by evaporated condensible matter, which exits the reaction chamber 12 as vapors through line 16i, and at least partially returns to the reaction chamber 12 as condensate through line 16ii. In this example, the majority of vapors exiting the reaction chamber 12 are cyclohexane, acetic acid, and water. The column 18 is designed, by well known to the art techniques, in a manner that, for all practical purposes, substantially all the acetic acid in the vapors exiting through line 16i is condensed in the first column 18 and returns to the reaction chamber 12 through line 16ii. For all practical purposes, the majority of the cyclohexane and substantially all the water in the vapors exiting the reaction chamber 12, pass through the first column 18, are condensed in the condenser 20, and are separated in the decanter 22. The column enables the withdrawal of substantially pure water through line 22iii. The condensed cyclohexane is at least partially returned to the top of the column 18 through line 18ii. As it moves downward, it causes condensation of the acetic acid, and they both return to the reaction chamber 12 through line 16ii. An adequate amount of water is preferably recycled, or fresh water added, to the reaction chamber 12, so that the catalyst remains in solution under the operation conditions. At the same time the amount of water recycled or added, should preferably be low enough, so that substantially a single liquid phase is present in the reaction zone 14 of the reaction chamber 12. Formation or existence of a second liquid phase in the reaction zone 14 reduces considerably the reaction rate and reactivity.

Off-gases are removed from line 22i through valve 22'. The majority of off-gases comprises mainly non-condensible gases, usually nitrogen, oxygen, carbon dioxide, carbon monoxide, etc. for example, with minor amounts of condensible matter, comprising for example such vapors as cyclohexane, acetic acid, water, etc. Recycling of gases (not shown) from line 22i to the reaction chamber 12 is many times desirable in order to improve sparging and mixing, to conserve oxygen, to reduce treatment requirements of the final off-gases, etc.

The valve 22" may be used in order to remove a sample, or part of the cyclohexane, if so desired.

The reaction mixture, having reached a steady state at a predetermined operation temperature, pressure, and desired conversion in the reaction zone 14 of the reaction chamber 12, is preferably continuously being removed from line 16iii as a reaction mixture stream. This stream is directed to a catalyst precipitation assembly, which comprises the elements between the reaction chamber 12 and the optional cooler 36, shown in FIG. 1. The catalyst precipitation assembly comprises at least one of thermal treatment means, such as the optional heater 24 for example, and de-watering means, such as the assembly of elements between the optional heater 24 and the first solids separator 34 for example, as shown in FIG. 1. It is highly preferable that both the thermal treatment means and the de-watering means are present and utilized for the catalyst precipitation, as illustrated in FIG. 1.

If the water level is rather low in the reaction zone 14, the cyclohexane level is rather high, and the catalyst level is rather high, just raising the temperature of the stream from its initial operation temperature to a higher temperature, may cause precipitation of catalyst. In such a case, precipitation may also be caused, even without raising the temperature, by simply removing water in the de-watering chamber 26. However, the utilization of the combination of both, the thermal treatment means and the de-watering means, is highly preferable.

Thus, in the case of adipic acid production for example, if the operation temperature in the reaction zone 14 is 100° C. for example, the temperature of the reaction stream may be raised by the optional heater 24, to a temperature preferably in the range of 110 to 150° C. The temperature to which the stream is raised is preferably kept lower tha a temperature at which catalyst precipitates at the water level of the stream. The higher temperature stream is then directed to the de-watering chamber 26. The temperature in the de-watering chamber 26, which may be different than that of stream 24i, is kept in the desired range by provision of heat to it. For example, heat may be provided to the de-watering chamber 26 by heating coils (not shown), inside or outside the de-watering chamber 26, or by re-circulating at least part of the contents of the chamber 26 through heater 24 back to the de-watering chamber 26, or through an additional heater (not shown), or by passing part of the filtrate from line 34i through a heater (not shown) or vaporizer (not shown) and directing it back to the de-watering chamber 26, or by any other technique well known to the art.

Adding heat to the contents of the de-watering chamber 26 is very important in order to continue evaporating cyclohexane, which azeotropically or otherwise removes water from the contents of the de-watering chamber 26, as the azeotrope or other vapor mixture passes through the second distillation column 28 in the same manner as already described for the first distillation column 18. The combination of cyclohexane/water is condensed in the condenser 30, and the cyclohexane is separated from the water in the decanter 32. Cyclohexane is directed back to the to the top of the distillation column 28, and finally returns to the de-watering chamber 26.

The level of water in the de-watering chamber 26 is maintained at a low equilibrium value at which catalyst precipitates at the temperature prevailing in the de-watering chamber 26. Preferably, substantially all the water, which influences the catalyst precipitation process, is removed.

In order to facilitate further catalyst precipitation in any precipitation chamber, hydrocarbon, such as cyclohexane for example, may also be added to the chamber.

More than one de-watering chambers with respective distillation columns, and respective or common condensers and decanters may be used, preferably in series, for higher removal of water.

It is important to note that the ratio of vapor flow through line 26i to the matter flow entering the chamber 26 through line 24i, and exiting through line 26iii, is of extreme importance, and it should be kept as high as technically and economically possible, for a higher degree of de-watering. In order to achieve the same de-watering degree at a lower ratio, an anhydride, such as acetic acid anhydride may be added, preferably continuously, in the chamber 26. Preferably, most of the de-watering is performed by the column, and the rest is performed by the anhydride.

A slurry containing the precipitated catalyst is directed, preferably in a continuous stream, through line 26iii to the first solids separator 34, where the precipitated catalyst is separated and removed through line 34ii. The filtrate is cooled down either by the optional cooler 36, or more preferably by flash crystallization in the crystallizer 38. Flash crystallization is conducted by pressure reduction through line 38i. During the pressure reduction, a large amount of cyclohexane with some acetic acid is evaporated from the mixture, causing a drastic temperature drop, so that the intermediate oxidation product, adipic acid in this example, precipitates and forms a slurry, which slurry is transferred, preferably continuously, to the second solids separator 40. The flashing process may be conducted in one or in multiple stages. The adipic acid is removed through line 40ii, while the filtrate is removed through line 40i for further treatment and/or recycling. The cyclohexane which is removed from line 38i is condensed, and preferably recycled to the reaction chamber 12 through feeding line 16, with or without pretreatment. The optional cooler 36 may be used by itself for cooling the mixture or it may be used in conjunction with the flash crystallization process. The optional cooler 36 may also be part of the crystallizer 38 for further cooling the contents of the crystallizer.

Due to substantial absence of water in the mixture entering the crystallizer 38, a second liquid phase is not usually formed. However, in case of a second liquid phase formation, a decanter (not shown) may be used, if so desired, to separate the polar from the non-polar phase, and then the adipic acid may be separated from the polar phase. Intentional addition of water after the first solids separator 34 in order to form a second liquid phase may be made, if so desired, followed by separation of the adipic acid from the polar phase.

Figure 2:
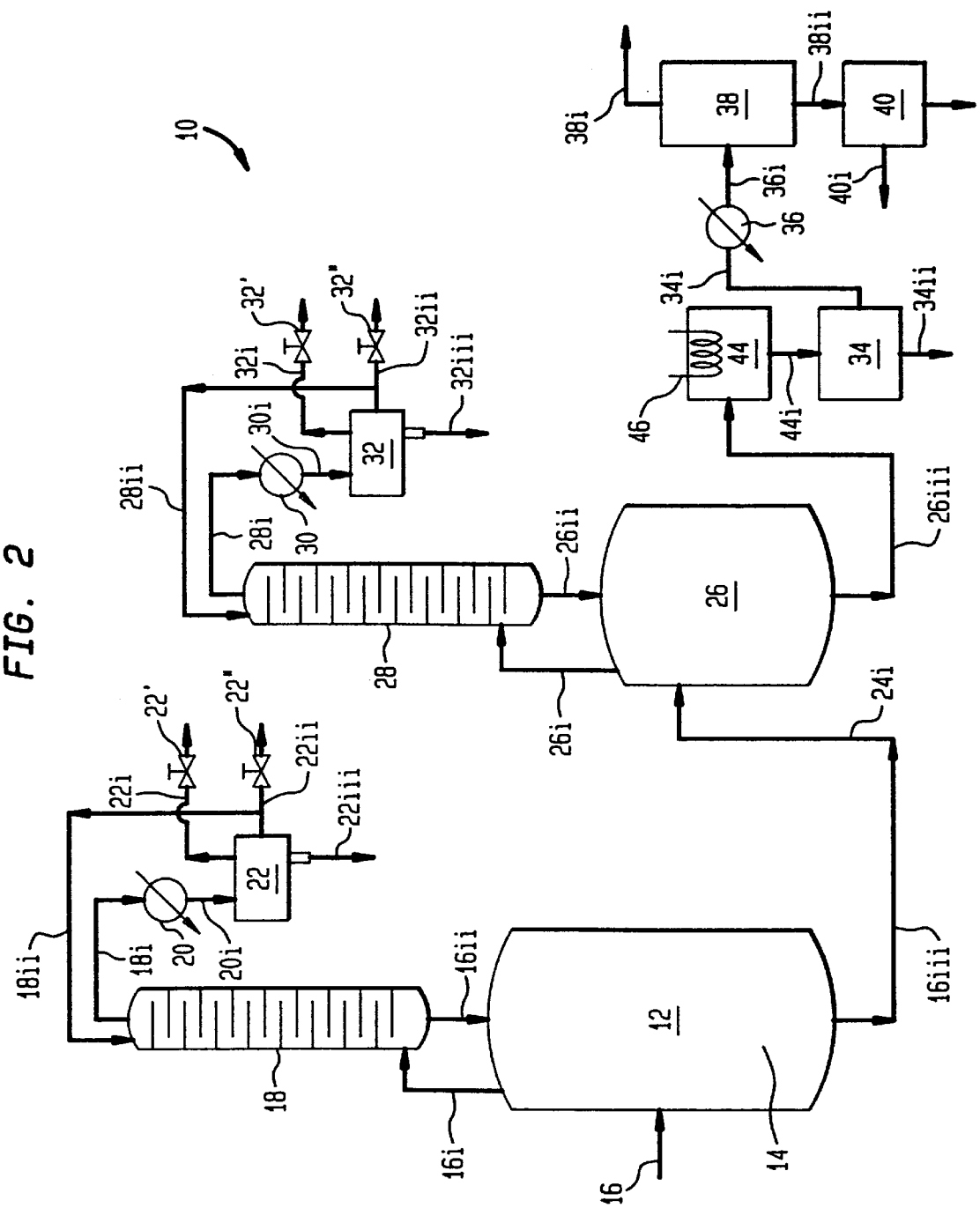
FIG. 2 illustrates a block diagram of another preferred embodiment of the present invention, wherein the thermal precipitation chamber is disposed after the de-watering chamber.

In another embodiment of the present invention, better illustrated in FIG. 2, there is provided a thermal precipitation chamber 44, which is heated by a heater 46. The thermal precipitation chamber 44 is disposed between the de-watering chamber 26 and the first solids separator 34. In addition, an optional cooler 42 replaces the optional heater 24 of the embodiment shown in FIG. 1. The rest of the elements involved in the embodiment of FIG. 2 are substantially the same as the ones illustrated in FIG. 1.

The operation of this embodiment is very similar to the operation of the embodiment illustrated in FIG. 1, with the following exceptions.

The stream of the reaction mixture leaving the reaction zone 14 of the reaction chamber 12 passes through line 16iii and it is introduced to the de-watering chamber 26. The temperature in the de-watering chamber 26 is controlled to be lower than the temperature at or over which catalyst precipitates at the water levels prevailing in chamber 26. The temperature may be lowered by evaporation of hydrocarbon and water and/or pressure reduction in chamber 26. In sequence, the de-watered mixture is transferred, preferably continuously, from the de-watering chamber 26 to the thermal precipitation chamber 44, where it is heated to or above the catalyst precipitation temperature, by means of the heater 46, and forms a precipitated catalyst slurry. Hydrocarbon, such as cyclohexane for example, may also be added to the chamber 44 for facilitating catalyst precipitation. The slurry is transferred, preferably continuously to the first solids separator 34, where, the precipitated catalyst is separated and leaves the separator 34 through line 34ii. The rest of the operation is similar to the operation of the embodiment illustrated in FIG. 1.

Figure 3:
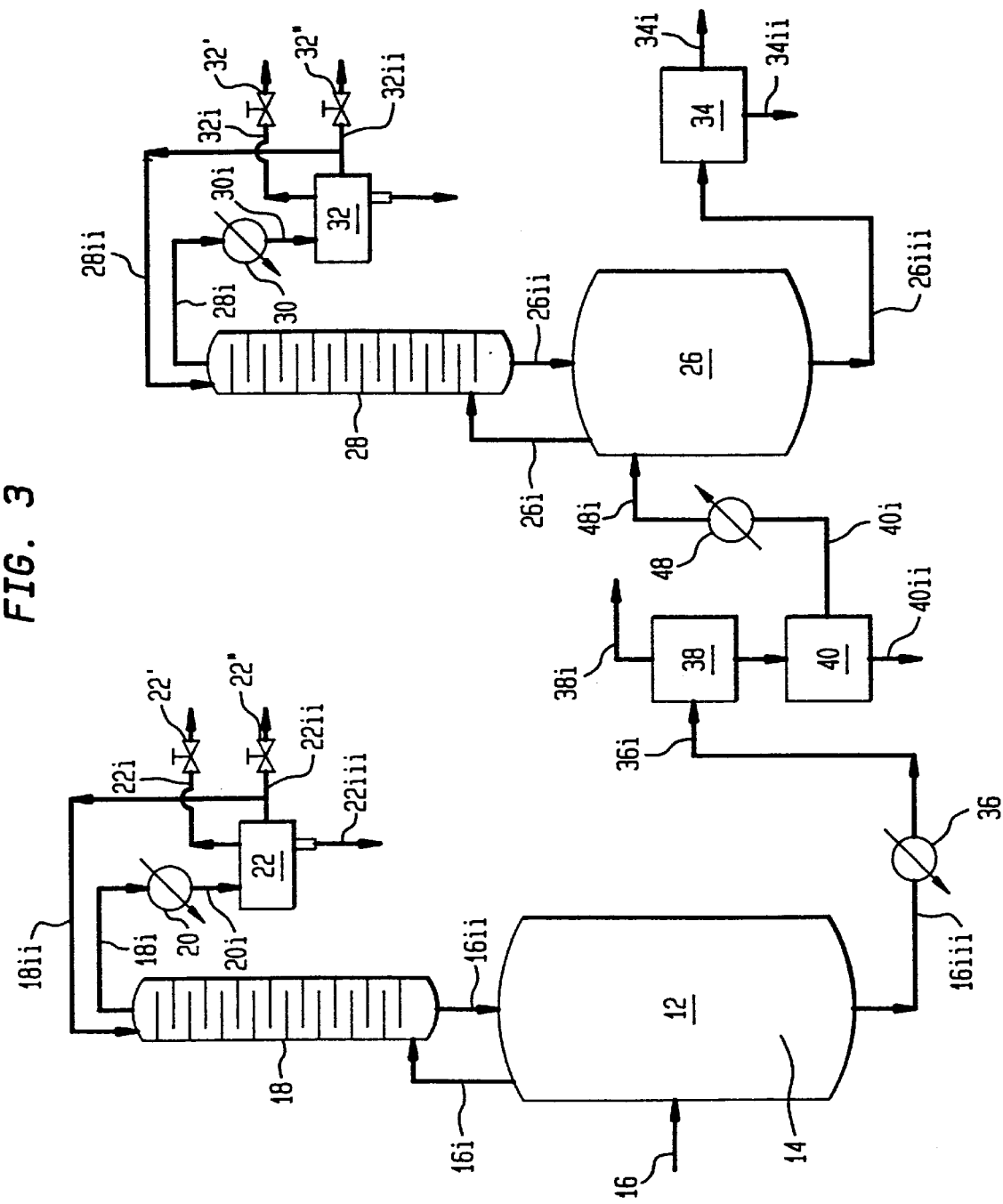
FIG. 3 illustrates a block diagram of another preferred embodiment of the present invention, wherein the intermediate oxidation product removal means are disposed between the reaction chamber and thermal precipitation chamber/de-watering chamber combination.

In still another embodiment of the present invention, better illustrated in FIG. 3, the optional cooler 36, the crystallizer 38, and the second solids separator 40 are positioned before the de-watering chamber 26. A heater 48 is also provided for raising the temperature of the stream passing through line 40i, before it enters the de-watering chamber 26 via line 48i. As in the previous cases, means (not shown) for heating the contents of the de-watering chamber 26 are necessary for the de-watering operation. Decanter(s) (not shown) may also be necessary in case of a second liquid phase formation. However, it is preferable that the operation of the embodiments of the present invention are conducted in a single liquid phase mode, if at all feasible.

The operation of this embodiment also is very similar to the operation of the embodiments illustrated in FIGS. 1 and 2, with the following exceptions.

The stream of the reaction mixture leaving the reaction zone 14 of the reaction chamber 12 through line 16iii, passes through the optional cooler 36. The purpose of the cooler 36 is to reduce the temperature of the stream to a low enough temperature so that the adipic acid will precipitate in the crystallizer 38. It is preferable that the cooling of the mixture in the crystallizer is performed by flash crystallization as the pressure is reduced through line 38i, as already discussed, in which case, the cooler 36 may not be needed, or may be used to provide some additional cooling. The crystallized adipic acid is removed in the second solids separator 40 through line 40ii, while the filtrate is heated to a temperature lower than a temperature at or over which catalyst precipitates at the water level prevailing in line 40i, but preferably higher than that at which or over which catalyst precipitates under the minimal levels of water in the de-watering chamber 26. The de-watering chamber 26 is also heated by heating means (not shown) for maintaining the temperature needed for catalyst precipitation. The slurry produced by catalyst precipitation is directed, as in the previous cases, to the first solids separator 34, where the precipitated catalyst is removed through line 34ii, while the filtrate is removed through line 34i for further treatment and/or recycling.

Figure 4:
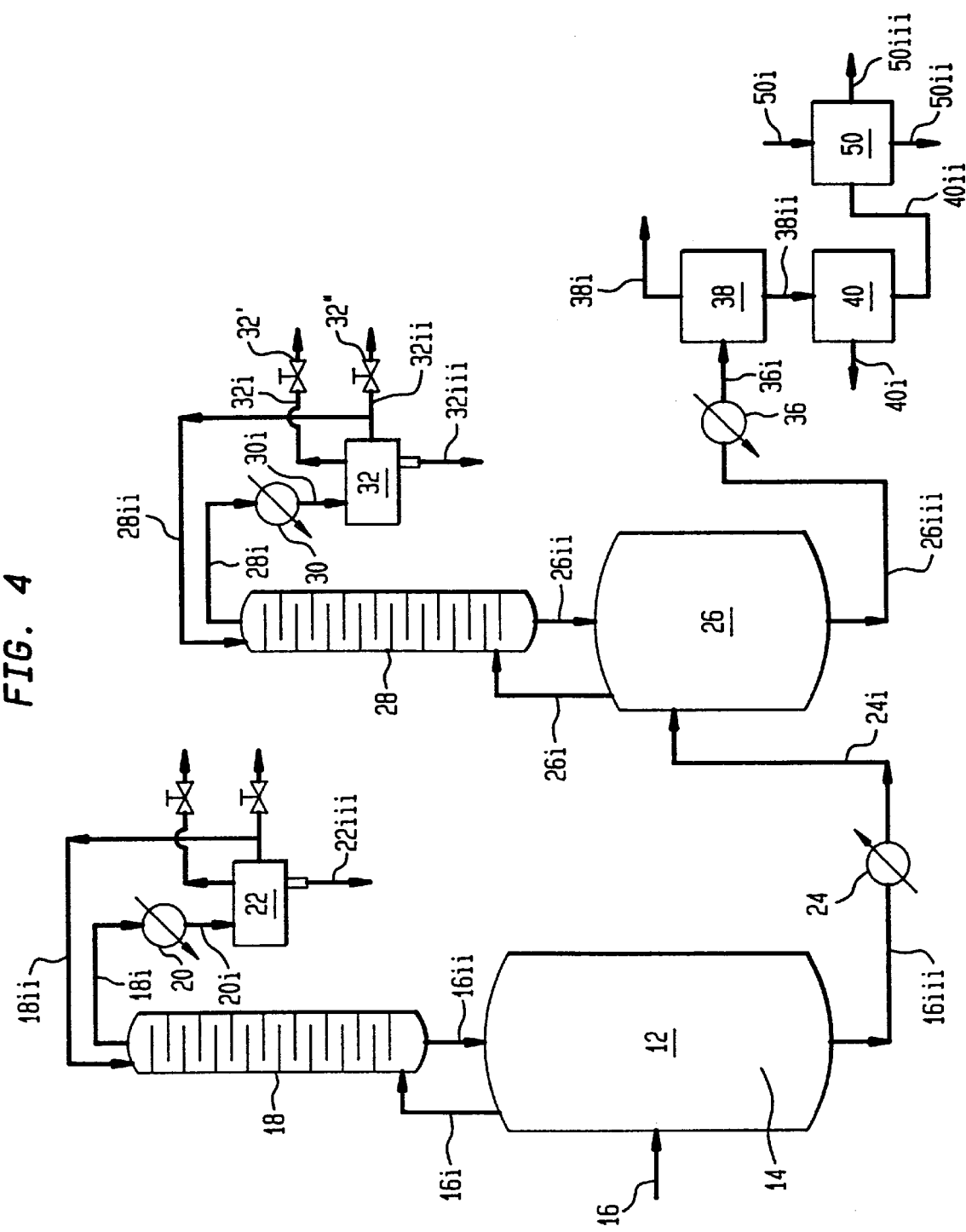
FIG. 4 illustrates a block diagram of another preferred embodiment of the present invention, wherein the water wash station is also utilized to remove catalyst from the intermediate oxidation product.

In still another embodiment of the present invention, better illustrated in FIG. 4, the adipic acid is precipitated in a slurry containing precipitated catalyst, and the catalyst is removed by washing the combined precipitate with water. This embodiment is similar to the embodiment illustrated in FIG. 1, except that the first solids separator 34 (see FIG. 1) is not present, and a solids water wash station 50 has been added and connected to the second solids separator 40 through line 40ii. A water incoming line 50i, a washed solids line 50ii, and a washings line 50iii are also connected to the water wash station 50.

The operation of this embodiment is substantially identical to the operation of the embodiment illustrated in FIG. 1, up to the point that the slurry of catalyst exits the de-watering chamber 26. At that point, the slurry, instead of being directed to a first solids separator, is directed to the optional cooler 36 and crystallizer 38. The intermediate oxidation product, adipic acid in this example, precipitates also within the catalyst slurry. The mixed precipitates of catalyst and adipic acid are separated from the filtrate in the second solids separator 40. The mixed solids are transferred, preferably continuously, to the water wash station 50, where they are washed with cold water entering through line 50i. The precipitated catalyst dissolves in the water, and the solution leaves the system through the washings line 50iii, while the adipic acid, being substantially insoluble in cold water, is removed through line 50ii. More than one water washing stations may be present. The solids may be carried on a belt (not shown) and progressively washed, so that substantially all the catalyst is dissolved and removed.

In still another embodiment, using the water wash station as described above, the crystallizer 38 and second separator 40 may be located before the de-watering chamber 26 in a manner similar to that described in the embodiment illustrated in FIG. 3.

Figure 5:
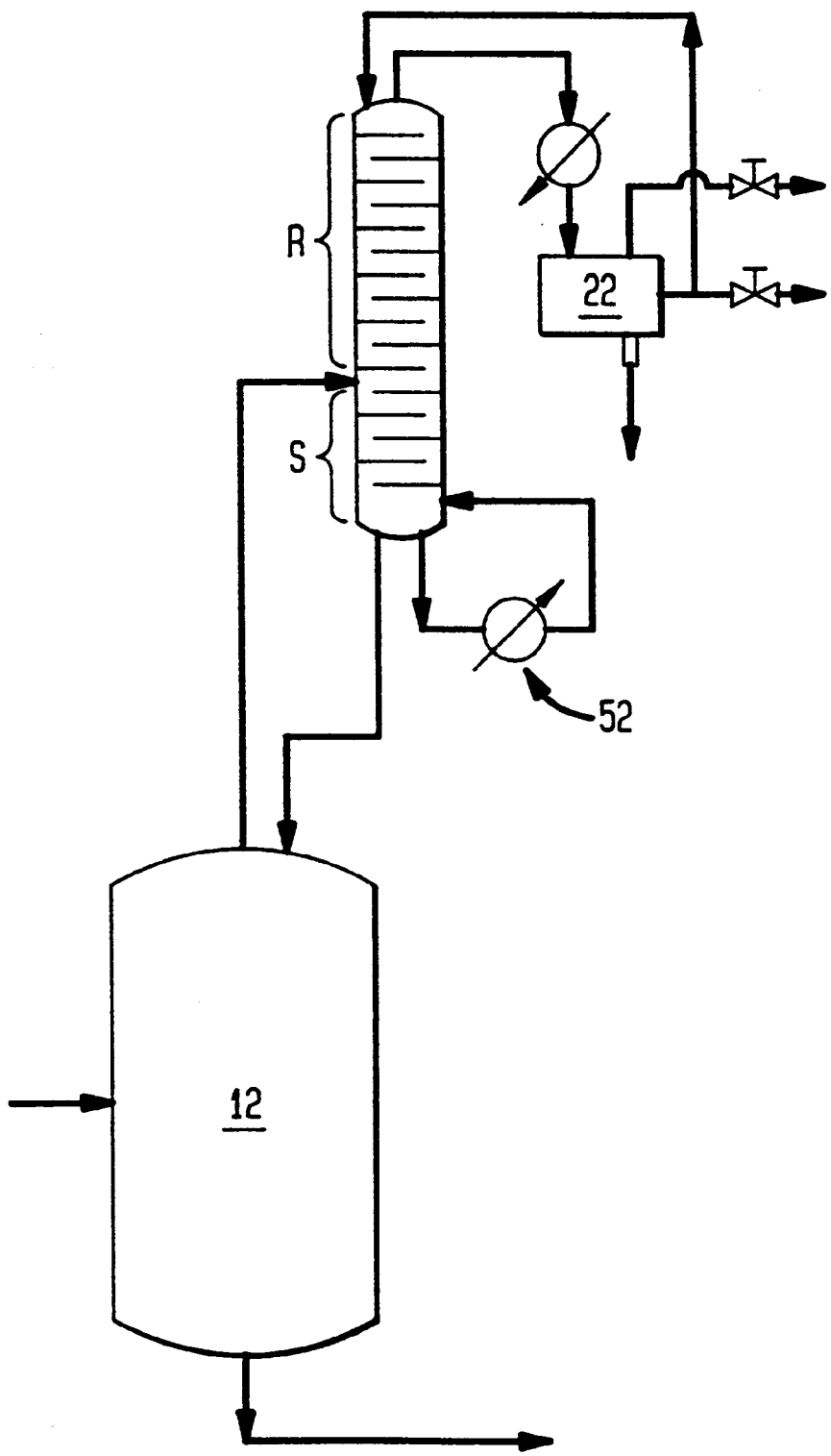
FIG. 5 illustrates a block diagram of a preferred distillation column, which may be used in conjunction with the reaction chamber or the de-watering chamber or any other appropriate chamber, or a combination thereof. This column is provided with a re-boiler, and is divided to a lower stripper zone and to an upper rectifier zone.

In the practice of this invention, it is highly preferable to use one or more distillation columns of the type shown in FIG. 5, which may replace column 18 and/or 28, shown in FIGS. 1 to 4. The distillation columns of this type are well known to the art. They have a stripper zone S and a rectifier zone R, above the stripper zone, as well as a re-boiler section 52, as shown in FIG. 5. They are characterized by better separation of the constituents entering the column, although they use more energy due to the additional re-boiler. Depending on particular case, the relative size of the two zones may vary considerably.

Figure 6:
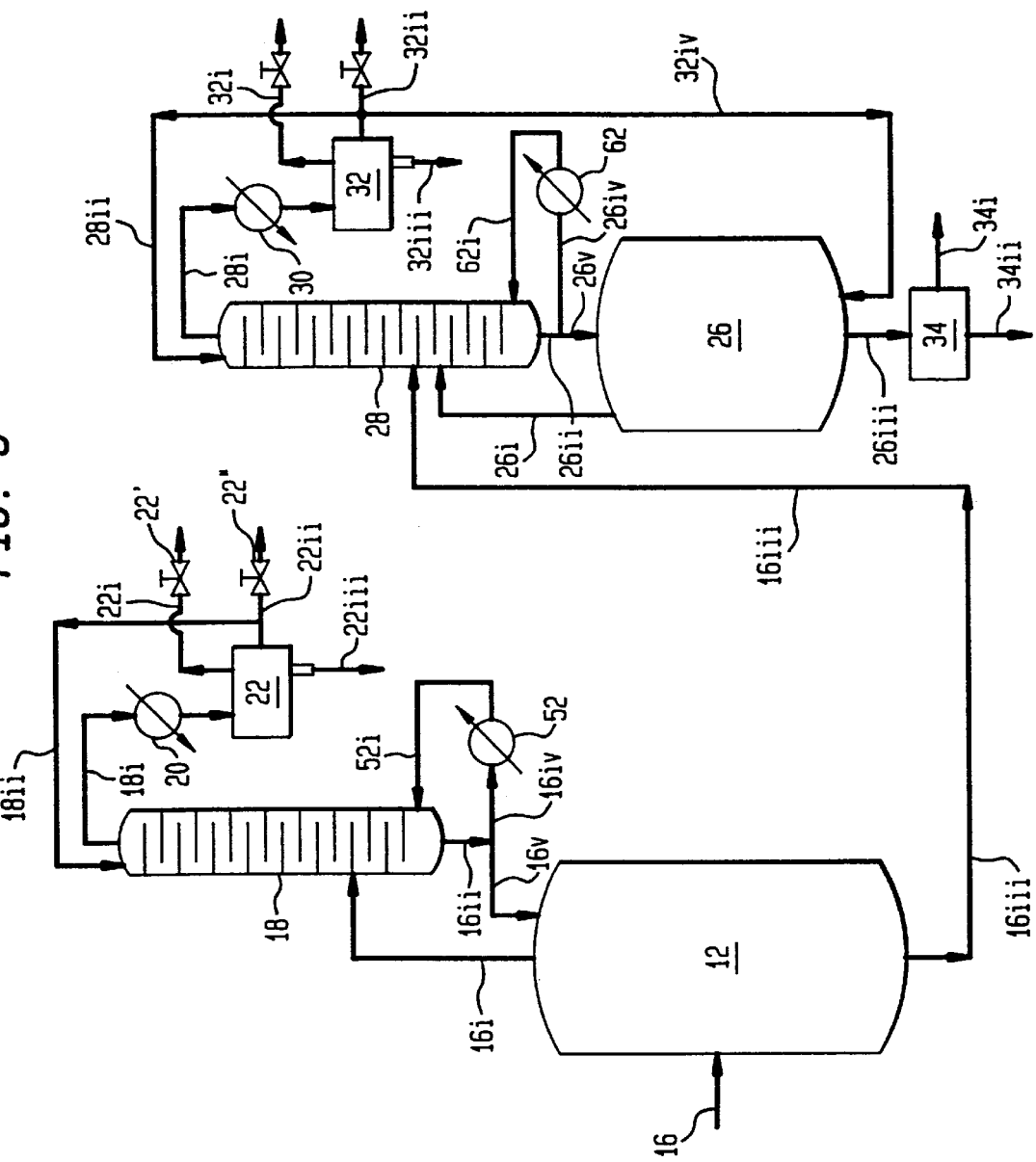
FIG. 6 illustrates a block diagram of another preferred embodiment of the present invention, which utilizes the preferred columns illustrated in FIG. 5. Catalyst precipitation takes place in a de-watering/precipitation chamber after removing most of the water in the column, and an additional adequate amount in the chamber to cause precipitation. The additional amount of water is removed by stripping or forming an azeotrope with hydrocarbon.

In another embodiment, better illustrated in FIG. 6, re-boilers 52 and 62 are added to the columns 18 and 28, respectively. In addition, line 16iii is directly connected to the column 28. The column 28 is connected to the precipitation chamber 26. Line 34iv is used for recycling hydrocarbon, such as cyclohexane for example, to the precipitation chamber 26 from the second decanter 32.

In operation of this embodiment, miscellaneous raw materials and recyclables, including in this example cyclohexane, acetic acid, cobalt compound catalyst, optional initiator (preferably cyclohexanone or acetaldehyde, or a mixture thereof), preferably water, and a gaseous oxidant, preferably comprising oxygen, enter the reaction zone 14, inside the reaction chamber 12, through the feeding means represented by line 16, in a similar manner as in the case of the embodiment illustrated in FIG. 1. Also similarly, the oxidation is preferably brought to a steady state. The majority of vapors exiting the reaction chamber 12 are cyclohexane, acetic acid, and water. The column 18, comprising in this case a stripper zone S and a rectifier zone R (see FIG. 5) is designed, by techniques well known to the art, in a manner that, for all practical purposes, substantially all the acetic acid in the vapors exiting through line 16i is condensed in the first column 18 and returns to the reaction chamber 12 through line 16ii, which in turn is followed by lines 16iv and 16v. Line 16v leads part of the condensed acetic acid back to the reaction chamber 12, while line 16iv leads the rest of the acetic acid to a re-boiler 52, and in turn close to the bottom of the stripper zone of the column 18. For all practical purposes, the majority of the cyclohexane and substantially all the water in the vapors exiting the reaction chamber 12, pass through the first column 18, are condensed in the condenser 20, and are separated in the decanter 22. Part of the condensed cyclohexane may be returned to the top of the column 18 through line 18ii. As it moves downward, it causes condensation of the acetic acid, which returns to the stripper zone. A controlled part of the condensed cyclohexane is returned to the reaction chamber 12 through line 22ii and valve 22". Also, a controlled amount of water is recycled in most cases to the reaction chamber 12 through line 22iii. Otherwise, a controlled amount of fresh water may be added to the reaction chamber 12, so that the catalyst remains in solution under the operation conditions. At the same time the amount of water recycled or added, should preferably be low enough, so that substantially a single liquid phase is present in the reaction zone 14 of the reaction chamber 12. Formation or existence of a second liquid phase in the reaction zone 14 reduces considerably the reaction rate and reactivity, as aforementioned.

The reaction mixture from the reaction chamber 12 is fed to the distillation column 28, as shown in FIG. 6. The catalyst contained in the reaction mixture, which enters the column 28, remains in the stripper zone as being non-volatile. The main liquid component in the stripper zone is acetic acid, which contains dissolved catalyst. Part of this solution is recycled through line 26iv and the re-boiler 62, while part of it is moved into the de-watering/precipitation chamber 26 through line 26v.

The degree of de-watering in the column 28, and the re-boiler loop 26ii–26iv–62–62i, is kept in a manner to ensure that the catalyst remains in solution, but close enough to the precipitation point, so that when the solution is treated in the de-watering/precipitation chamber 26, catalyst precipitation occurs. The treatment in the de-watering/precipitation chamber 26 comprises further de-watering, to a water level at which catalyst precipitates at the temperature maintained in the de-watering/precipitation chamber 26. The de-watering in the de-watering/precipitation chamber 26 is achieved by cyclohexane entering the chamber 26 through line 32iv, and exiting through line 26i as vapor containing water. A slurry containing the precipitated catalyst is directed, preferably in a continuous stream, through line 26iii to the first solids separator 34, where the precipitated catalyst is separated and removed through line 34ii. The rest of the operation is similar to the operation of the embodiments described earlier.

Figure 7:
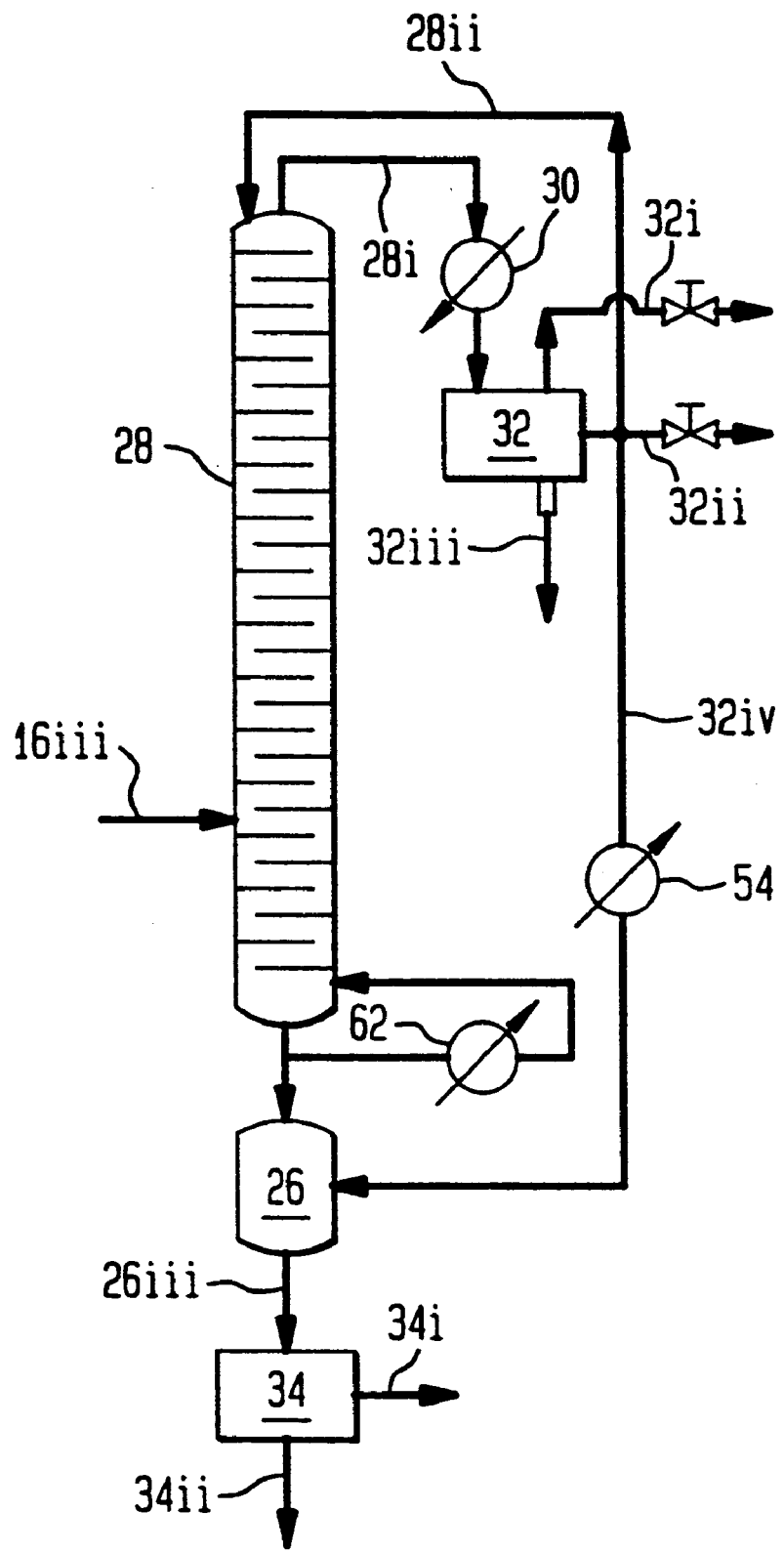
FIG. 7 illustrates a block diagram of another preferred embodiment of the present invention, which utilizes the preferred columns illustrated in FIG. 5. Catalyst precipitation takes place in a de-watering/precipitation chamber after removing an adequate amount of the water in the column, so that an appropriate amount of hydrocarbon added to the de-watering/precipitation chamber causes catalyst precipitation.

In another embodiment of the instant invention, better illustrated in FIG. 7, there is provided line 32iv, which transfers cyclohexane to the de-watering/precipitation chamber 26 after preferably passing the cyclohexane through a cyclohexane heater 54.

The operation of this embodiment is similar to the operation of the embodiment illustrated in FIG. 6, with the difference that no vapors of cyclohexane containing water are transferred from the chamber 26 to the column 28. The precipitation in this case is caused by the enrichment of the acetic acid solution of catalyst with cyclohexane. As mentioned earlier, the higher the level of cyclohexane in a solution containing catalyst, the higher the level of water at which catalyst precipitates.

Figure 8:
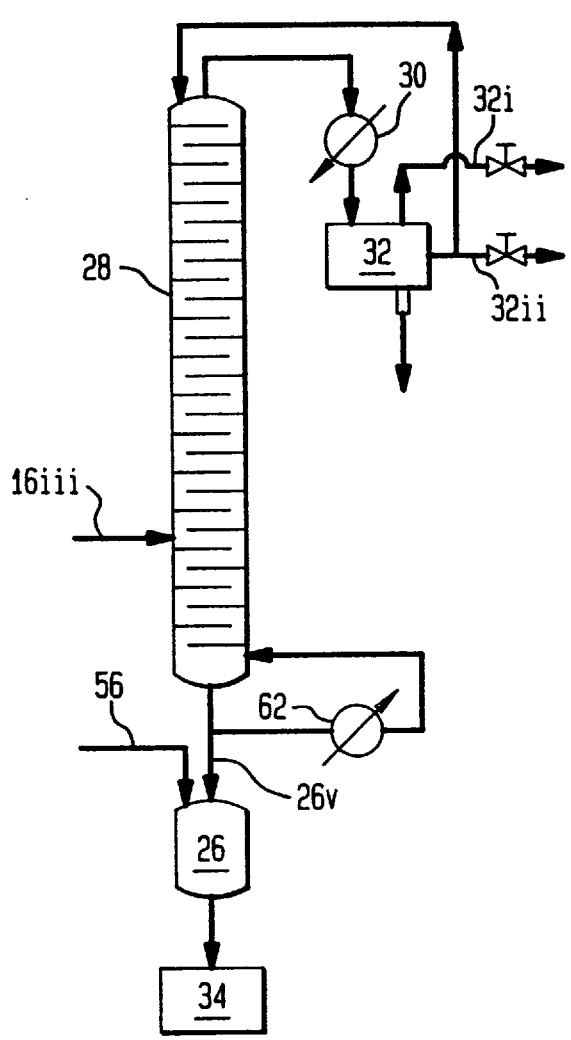
FIG. 8 illustrates a block diagram of another preferred embodiment of the present invention, which utilizes the preferred columns illustrated in FIG. 5. Catalyst precipitation takes place in a de-watering/precipitation chamber after removing most of the water in the column, and adding an appropriate amount of anhydride, such as acetic acid anhydride for example, to the de-watering/precipitation chamber which removes an additional amount of water by hydrolysis, and causes catalyst precipitation.

In another embodiment of the present invention, better illustrated in FIG. 8, there is provided a line 56 for introducing controlled amounts of an anhydride, such as acetic acid anhydride for example, or any other appropriate water removing substance.

The operation of this embodiment is similar to the operation of the embodiment illustrated in FIG. 7, with the difference that no vapors of cyclohexane containing water are transferred from the chamber 26 to the column 28, and no enrichment of the acetic acid solution of catalyst with cyclohexane is conducted. Instead, a small controlled amount of an anhydride, such as acetic acid anhydride for example, is introduced to the chamber 26 through line 56. Since the water level entering the chamber 26 is preferably controlled to be close to the catalyst precipitation level, only small amounts of acetic acid anhydride are required to reduce the water content of the solution entering the chamber 26 through line 26v, to the catalyst precipitation level. A stream (not shown) of hydrocarbon, such as cyclohexane for example, may also be introduced to chamber 44 in order to facilitate the catalyst precipitation process.

Figure 9:
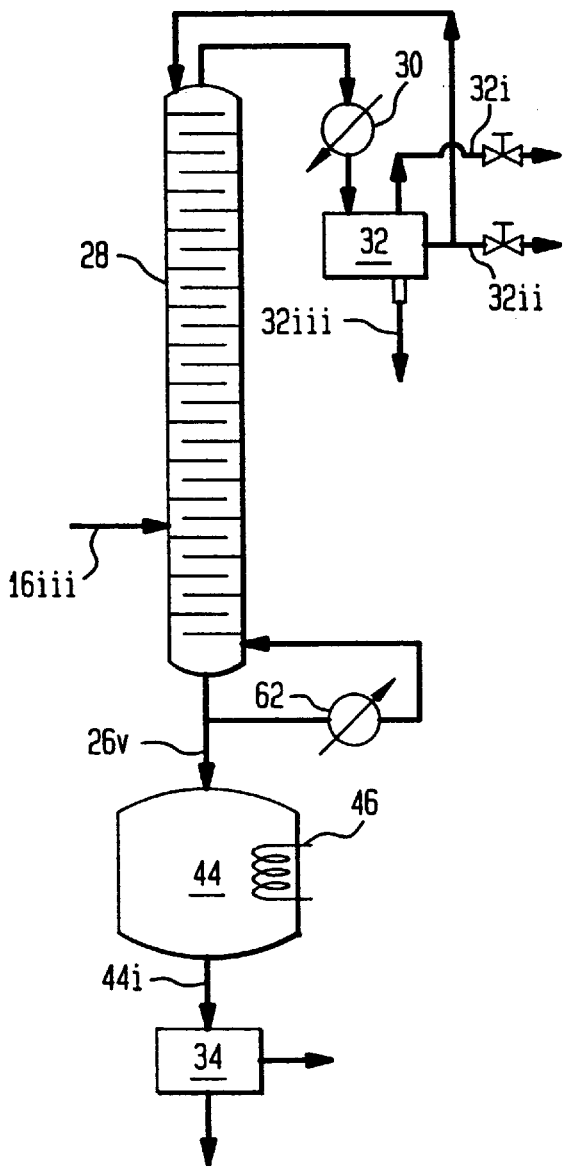
FIG. 9 illustrates a block diagram of another preferred embodiment of the present invention, which utilizes the preferred columns illustrated in FIG. 5. Catalyst precipitation takes place in a de-watering/precipitation chamber after removing an adequate amount of the water in the column at reduced temperature and pressure, so that temperature rise in the de-watering/precipitation chamber causes catalyst precipitation.

In another embodiment of the present invention, better illustrated in FIG. 9, there is provided a heater 46 for raising the temperature of the solution from the entry temperature through line 26v to an adequate degree that catalyst precipitation occurs. In order to have a reduced temperature in column 28, the pressure is reduced through line 32i. Since the precipitation chamber 44 operates at higher pressure and temperature, a pump (not shown) or other similar device forces the liquid into the precipitation chamber 44 through line 26v.

The operation of this embodiment is similar to the operation of the previous embodiment. The water level of the solution entering the chamber 44 is preferably controlled to be close to the catalyst precipitation level at the entry temperature, as discussed above. In the precipitation chamber 44, the temperature is raised by the heater 46 to a degree that catalyst precipitates, since at the higher temperatures, the level of water at or under which catalyst precipitates is raised.

Figure 10:
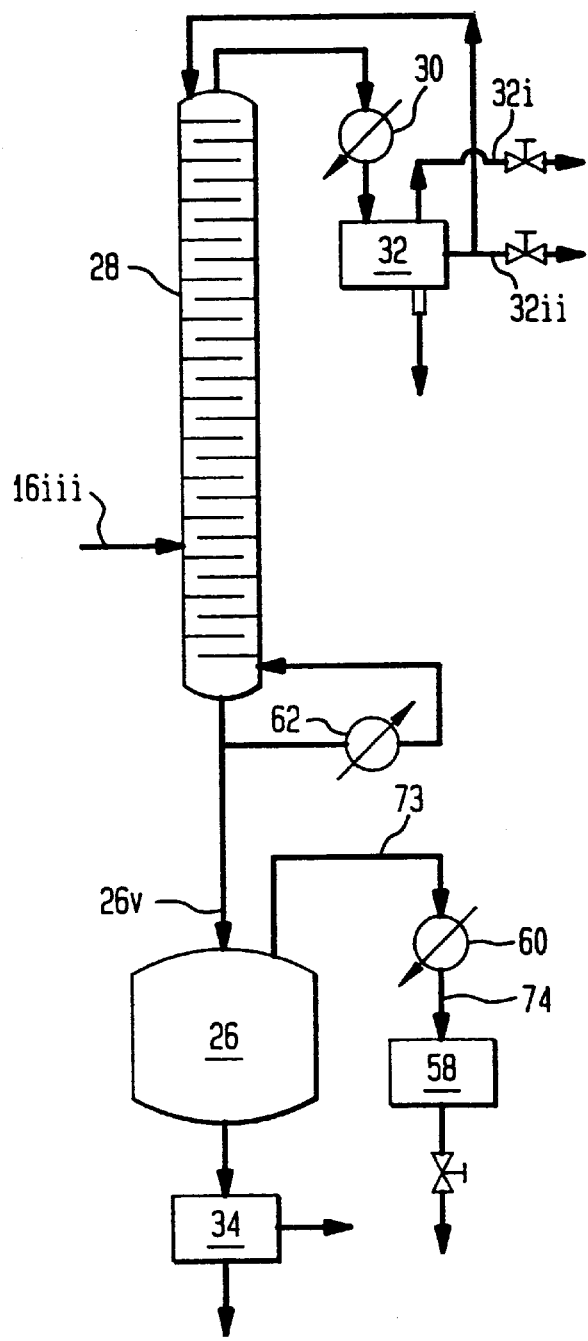
FIG. 10 illustrates a block diagram of another preferred embodiment of the present invention, which utilizes the preferred columns illustrated in FIG. 5. Catalyst precipitation takes place in a de-watering/precipitation chamber after removing most of the water in the column, and concentrating the mixture in the de-watering/precipitation chamber, along with removing at least part of the residual water.

In still another embodiment of the present invention, better illustrated in FIG. 10, there is provided a condenser 60, connected to the chamber 26 through line 73, and to vessel 58 through line 74.

The operation of this embodiment is similar to the operation of the previous embodiments. The water level of the solution entering the chamber 44 is preferably controlled to be close to the catalyst precipitation level at the operating temperature. The chamber 26 is heated by any appropriate means, and acetic acid vapors are transferred to the condenser 60, where they condense, and the acetic acid is collected in vessel 58, from which it may be further transferred to any desired portion of the reactor device. The acetic acid (along with residual water) removal from chamber 26 is controlled so that the concentration of catalyst is increased and the water level decreased to the point that catalyst precipitates, and removed in the first solids separator 34, as discussed for the previous embodiments.

Figure 11:
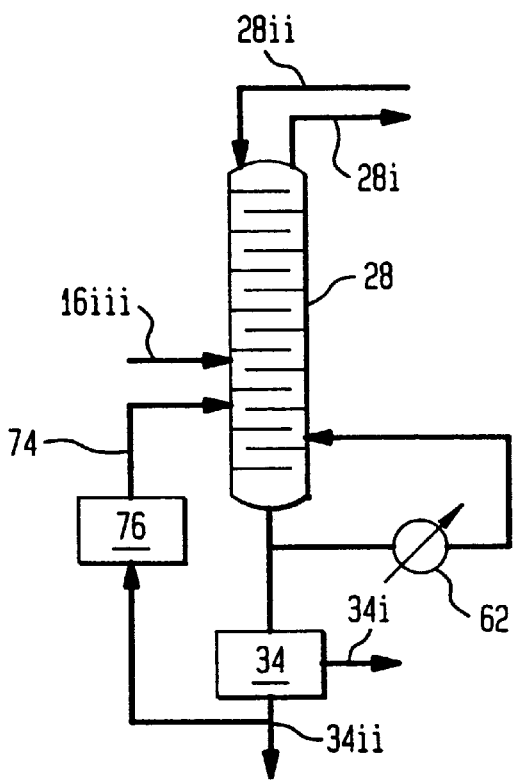
FIG. 11 illustrates a block diagram of another preferred embodiment of the present invention, which utilizes the preferred columns illustrated in FIG. 5. Catalyst precipitation takes place in the column and in the re-boiler. Recycling of a small amount of separated catalyst crystals provides seeds/sites for crystal growth and prevention or reduction of catalyst deposition on solid surfaces.

In another embodiment, better illustrated in FIG. 11, de-watering in column 28 is controlled to the point that catalyst precipitates within the column 28 and the re-boiler 62. In order to prevent or minimize adhering of catalyst to the solid surfaces of the column and the re-boiler, it is preferable to recycle a small amount (nominally 5–10%) of the crystals separated through line 34ii, back to the column 28 via line 74. Line 74 is preferably positioned at such level of the column that no substantial dissolution of the catalyst crystals occurs. The crystals provide seeds/sites for crystal growth and prevent, or minimize, or at least reduce catalyst deposition on the solid surfaces of the column and the re-boiler. On many occasions, it is preferable to use a grinder 76 for grinding the crystals of the catalyst returning to the column 28 to a smaller size. Seeds from other sources may also be used. These seeds may comprise catalyst or may comprise other substances suitable for providing catalyst crystallization sites.

Figure 12:
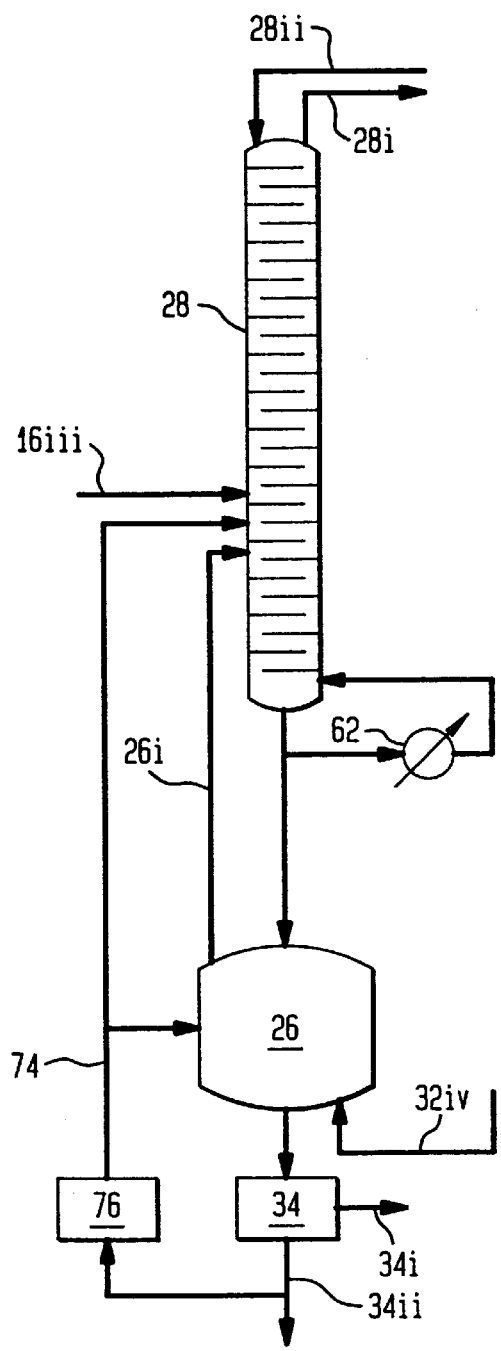
FIG. 12 illustrates a block diagram of another preferred embodiment of the present invention, which utilizes the preferred columns illustrated in FIG. 5. Catalyst precipitation takes place partially in the column and in the re-boiler, and partially in the de-watering/precipitation chamber. Recycling of a small amount of separated catalyst crystals provides seeds/sites for crystal growth and prevention or reduction of catalyst deposition on solid surfaces.

In another embodiment, better illustrated in FIG. 12, and similar to the embodiment illustrated in FIG. 6, partial precipitation is induced in the column 28 and the re-boiler 62 and partial precipitation is induced in the de-watering/precipitation chamber 26. Preferably, a minor amount of precipitation (e.g., 5–20%) is caused to take place in the column 28 and re-boiler 62, and the rest in the de-watering/precipitation chamber 26. Preferably, in this case also, a small amount (nominally 5–10%) of the crystals separated through line 34ii, are recycled back to the column 28 via line 74, and more preferably they are ground to a rather uniform smaller size by passing through grinder 76. The re-boiler loop may be omitted, if so desired, in which case, the column is driven by the vapor entering the column through line 26i.

Figure 13:
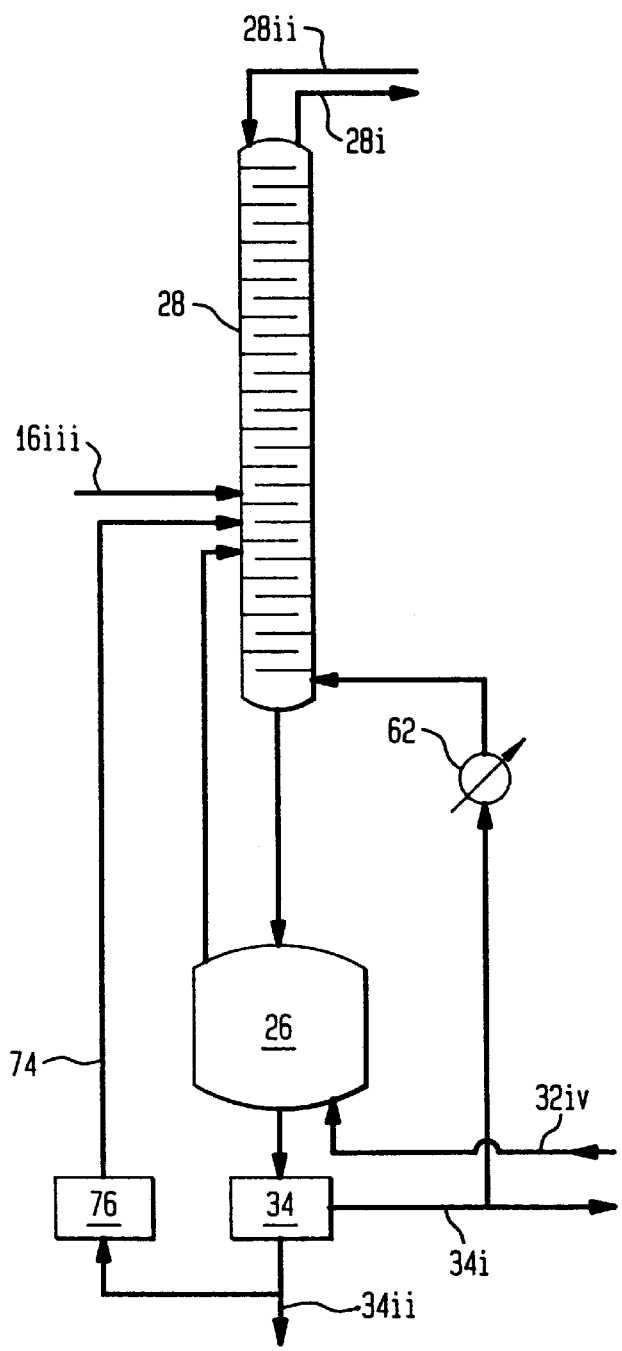
FIG. 13 illustrates a block diagram of another preferred embodiment of the present invention, which utilizes the preferred columns illustrated in FIG. 5. Catalyst precipitation takes place partially in the column, and partially in the dewatering/precipitation chamber. The re-boiler is provided with solution after removal of the precipitated catalyst.
Figure 14:
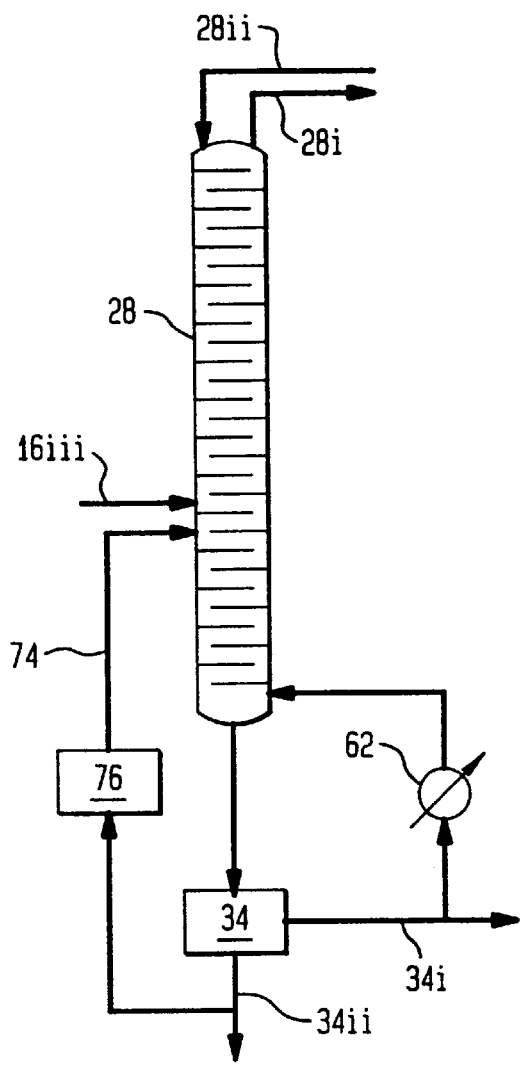
FIG. 14 illustrates a block diagram of another preferred embodiment of the present invention, which utilizes the preferred columns illustrated in FIG. 5. Catalyst precipitation takes place in the column. The re-boiler is provided with solution after removal of the precipitated catalyst.

In another embodiment, better illustrated in FIG. 14, and similar to the embodiment illustrated in FIG. 13, the re-boiler 62 is also fed from line 34i, which contains no catalyst crystals, but the total catalyst precipitation takes place in the column 28.

Figure 15:
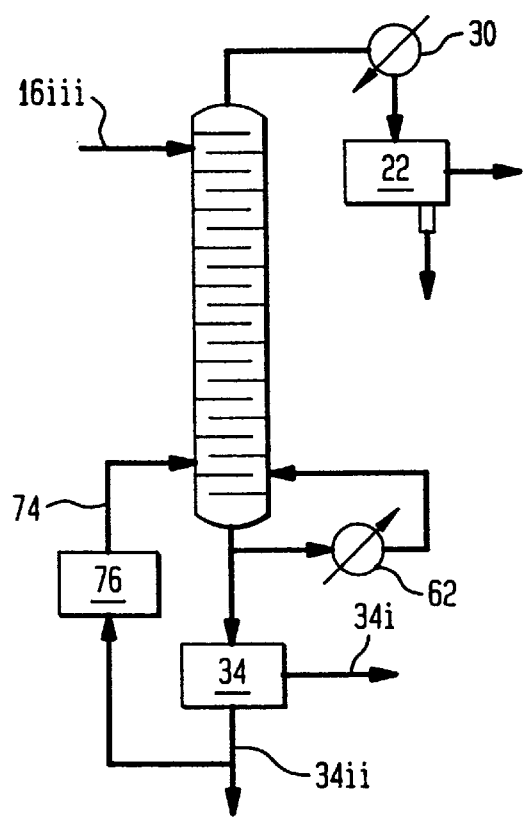
FIG. 15 illustrates a block diagram of another preferred embodiment of the present invention, which utilizes the preferred column illustrated in FIG. 5, in which, however, the upper rectification portion has been substantially eliminated.

In still another embodiment, better illustrated in FIG. 15, line 16iii enters the column at a higher portion, so that the rectification zone is eliminated or greatly reduced. Two phases are formed in the decanter 22 from vapors condensed in condenser 30. An upper non-polar phase contains mainly cyclohexane with minor amounts of acetic acid and water, while a lower polar phase contains mainly water and acetic acid with minor amounts of cyclohexane. The two phases are separated and treated in any desirable manner, depending on the details of the process. The catalyst precipitation takes place in the column and in the re-boiler, as in other embodiments.

A series of more than one columns may also be used, if so desired, in order to achieve a higher de-watering degree before precipitation in a camber such as chamber 26, or chamber 44, or any other appropriate chamber. A single multi-stage column, having an effect of more than one columns arranged in series may also be used. Further, columns in parallel may be used to increase the total flow in the system, while maintaining a rather low flow in each column.

It should be understood that according to the present invention, any liquids or gases or off-gases may be recycled totally or partially from any section to any other section, if so desired. Further, any combinations of the exemplifying embodiments, in part or in total, or any equivalent arrangements or any combinations of equivalent arrangements may be utilized, and are within the scope of the present invention.

Although miscellaneous functions are preferably controlled by a computerized controller, it is possible, according to this invention, to utilize any other type of controller or even manual controls and/or labor for controlling one or more functions. Preferred computerized controllers are artificially intelligent systems (expert systems, neural networks, and fuzzy logic systems, well known to the art). Of the three types of the artificially intelligent systems, the neural network, which is a learning system, collects information from different places of the device (for example pressure, temperature, chemical or other analysis, etc.), stores this information along with the result (pressure drop rate, reaction rate, reactivity, and the like, for example), and is programmed to use this information in the future, along with other data if applicable, to make decisions regarding the action to be taken at each instance. The expert systems are programmed based on the expertise of experienced human beings. The fuzzy logic systems are based on intuition rules in addition to expertise rules.

Oxidations according to this invention, are non-destructive oxidations, wherein the oxidation product is different than carbon monoxide, carbon dioxide, and a mixture thereof, such as adipic acid for example. Of course, small amounts of these compounds may be formed along with the oxidation product, which may be one product or a mixture of products.

Examples include, but of course, are not limited to preparation of C5–C8 aliphatic dibasic acids from the corresponding saturated cycloaliphatic hydrocarbons, such as for example preparation of adipic acid from cyclohexane. Examples of aromatic carboxylic acids are benzoic acid, phthalic acid, isophthalic acid, and terephthalic acid, among others.

Regarding adipic acid, the preparation of which is especially suited to the methods and apparatuses of this invention, general information may be found in a plethora of U.S. Patents, among other references. These include, but are not limited to:

U.S. Pat. Nos. 2,223,493; 2,589,648; 2,285,914; 3,231,608; 3,234,271; 3,361,806; 3,390,174; 3,530,185; 3,649,685; 3,657,334; 3,957,876; 3,987,100; 4,032,569; 4,105,856; 4,158,739 (glutaric acid); U.S. Pat. Nos. 4,263,453; 4,331,608; 4,606,863; 4,902,827; 5,221,800; and 5,321,157.

Diacids (for example adipic acid, phthalic acid, isophthalic acid, terephthalic acid, and the like) or other suitable compounds may be reacted, according to well known to the art techniques, with a third reactant selected from a group consisting of a polyol, a polyamine, and a polyamide in a manner to form a polymer of a polyester, or a polyamide, or a (polyimide and/or polyamideimide), respectively. Preferably the polyol, the polyamine, and the polyamide are mainly a diol, a diamine, and a diamide, respectively, in order to avoid excessive cross-linking. The polymer resulting from this reaction may be spun by well known to the art techniques to form fibers.

Examples demonstrating the operation of the instant invention have been given for illustration purposes only, and should not be construed as limiting the scope of this invention in any way. In addition it should be stressed that the preferred embodiments discussed in detail hereinabove, as well as any other embodiments encompassed within the limits of the instant invention, may be practiced individually, or in any combination thereof, according to common sense and/or expert opinion. Individual sections of the embodiments may also be practiced individually or in combination with other individual sections of embodiments or embodiments in their totality, according to the present invention. These combinations also lie within the realm of the present invention. Furthermore, any attempted explanations in the discussion are only speculative and are not intended to narrow the limits of this invention.

What is claimed is:

1. A method of removing catalyst from a mixture comprising the catalyst and water, the mixture having been formed after reaction of a hydrocarbon with an oxidant to form an intermediate oxidation product at an operation temperature, in the presence of the catalyst, and water at a first water level, the method being characterized by steps:
    (a) changing the operation temperature to a temperature at or above a precipitation temperature, at which and over which precipitation temperature, the catalyst in the mixture would precipitate, at least partially, if the water level in the mixture had been reduced to or under a precipitation water level;
    (b) removing an adequate amount of water from the mixture, in order to bring the water level to or under the precipitation water level, thereby causing the catalyst to precipitate, at least partially; and
    (c) removing the precipitated catalyst from the rest of the mixture.

2. A method as defined in claim 1, wherein substantially all the water, which influences the catalyst precipitation process, is removed.

3. A method as defined in claim 1, further comprising a step of removing at least partially the intermediate oxidation product before at least partial removal of catalyst.

4. A method as defined in claim 1, further comprising a step of removing at least partially the intermediate oxidation product after at least partial removal of catalyst.

5. A method as defined in claim 2, further comprising a step of removing at least partially the intermediate oxidation product before at least partial removal of catalyst.

6. A method as defined in claim 2, further comprising a step of removing at least partially the intermediate oxidation product after at least partial removal of catalyst.

7. A method as defined in claim 1, wherein step (c) comprises a step selected from a group consisting of centrifuging, filtering, and a combination thereof.

8. A method as defined in claim 2, wherein step (c) comprises a step selected from a group consisting of centrifuging, filtering, and a combination thereof.

9. A method as defined in claim 1, further comprising a step of forming a precipitate containing both precipitated intermediate oxidation product and catalyst, and a step of dissolving the precipitated catalyst in water.

10. A method as defined in claim 2, further comprising a step of forming a precipitate containing both precipitated intermediate oxidation product and catalyst, and a step of dissolving the precipitated catalyst in water.

11. A method as defined in claim 1, wherein the water is removed in at least two stages, a first stage at which most of a desired amount of water is removed, and a second stage at which the rest of the desired amount of water is removed.

12. A method as defined in claim 11, wherein the water in the second stage is removed by stripping or forming an azeotrope with the hydrocarbon.

13. A method as defined in claim 11, wherein the water in the second stage is removed by addition of an acid anhydride.

14. A method as defined in claim 13, wherein the acid anhydride is acetic acid anhydride.

15. A method as defined in claim 11, wherein the water in the second stage is removed by distillation with simultaneous concentration of the mixture containing the catalyst and the water.

16. A method as defined in claim 2, wherein the water is removed in at least two stages, a first stage at which most of the water is removed, and a second stage at which the rest of the water is substantially removed.

17. A method as defined in claim 16, wherein the water in the second stage is removed by stripping or forming an azeotrope with the hydrocarbon.

18. A method as defined in claim 16, wherein the water in the second stage is removed by addition of an acid anhydride.

19. A method as defined in claim 18, wherein the acid anhydride is acetic acid anhydride.

20. A method as defined in claim 16, wherein the water in the second stage is removed by distillation with simultaneous concentration of the mixture containing the catalyst and the water.

21. A method as defined in claim 1, wherein deposition of catalyst on solid surfaces is reduced, and/or catalyst precipitation is assisted by use of seeds added to the mixture.

22. A method as defined in claim 21, wherein the seeds comprise precipitated catalyst.

23. A method as defined in claim 2, wherein deposition of catalyst on solid surfaces is reduced, and/or catalyst precipitation is assisted by use of seeds added to the mixture.

24. A method as defined in claim 23, wherein the seeds comprise precipitated catalyst.

25. A method as defined in claim 1, wherein the catalyst precipitation is conducted in at least two stages.

26. A method as defined in claim 2, wherein the catalyst precipitation is conducted in at least two stages.

27. A method as defined in claim 1, wherein the hydrocarbon comprises cyclohexane or is substituted by a compound selected from a group consisting of cyclohexanone, cyclohexanol, cyclohexylhydroperoxide, o-xylene, m-xylene, p-xylene, a mixture of at least two of cyclohexane, cyclohexanone, cyclohexanol, cyclohexylhydroperoxide, and a mixture of at least two of o-xylene, m-xylene, p-xylene;
    the oxidant comprises oxygen; and
    a major portion of the intermediate oxidation product comprises a compound selected from a group consisting of adipic acid, cyclohexanol, cyclohexanone, cyclohexylhydroperoxide, phthalic acid, isophthalic acid, terephthalic acid, a mixture of at least two of adipic acid, cyclohexanone, cyclohexanol, and cyclohexylhydroperoxide, and a mixture of at least two of phthalic acid, isophthalic acid, and terephthalic acid.

28. A method as defined in claim 2, wherein the hydrocarbon comprises cyclohexane or is substituted by a compound selected from a group consisting of cyclohexanone, cyclohexanol, cyclohexylhydroperoxide, o-xylene, m-xylene, p-xylene, a mixture of at least two of cyclohexane, cyclohexanone, cyclohexanol, cyclohexylhydroperoxide, and a mixture of at least two of o-xylene, m-xylene, p-xylene;

the oxidant comprises oxygen; and a major portion of the intermediate oxidation product comprises a compound selected from a group consisting of adipic acid, cyclohexanol, cyclohexanone, cyclohexylhydroperoxide, phthalic acid, isophthalic acid, terephthalic acid, a mixture of at least two of adipic acid, cyclohexanone, cyclohexanol, and cyclohexylhydroperoxide, and a mixture of at least two of phthalic acid, isophthalic acid, and terephthalic acid.

29. A method as defined in claim 1, wherein the catalyst comprises a metal compound, the metal selected from a group consisting of Cu, Ag, Au, Mg, Ca, Sr, Ba, Zn, Cd, Hg, Al, Sc, Y, Ga, In, Tl, Ti, Zr, Hf, Ge, Sn, Pb, V, Nb, Ta, Cr, Mo, W, Mn, Tc, Re, Fe, Ru, Os, Co, Rh, Ir, Ni, Pd, Pt, and a combination thereof.

30. A method as defined in claim 2, wherein the catalyst comprises a metal compound, the metal selected from a group consisting of Cu, Ag, Au, Mg, Ca, Sr, Ba, Zn, Cd, Hg, Al, Sc, Y, Ga, In, Tl, Ti, Zr, Hf, Ge, Sn, Pb, V, Nb, Ta, Cr, Mo, W, Mn, Tc, Re, Fe, Ru, Os, Co, Rh, Ir, Ni, Pd, Pt, and a combination thereof.

31. A method as defined in claim 1, wherein the intermediate oxidation product comprises adipic acid, the hydrocarbon comprises cyclohexane, the catalyst comprises a cobalt compound, the gaseous oxidant comprises oxygen, and the mixture comprises acetic acid.

32. A method as defined in claim 2, wherein the intermediate oxidation product comprises adipic acid, the hydrocarbon comprises cyclohexane, the catalyst comprises a cobalt compound, the gaseous oxidant comprises oxygen, and the mixture comprises acetic acid.

33. A method as defined in claim 3, wherein the intermediate oxidation product comprises adipic acid, the hydrocarbon comprises cyclohexane, the catalyst comprises a cobalt compound, the gaseous oxidant comprises oxygen, and the mixture comprises acetic acid.

34. A method as defined in claim 4, wherein the intermediate oxidation product comprises adipic acid, the hydrocarbon comprises cyclohexane, the catalyst comprises a cobalt compound, the gaseous oxidant comprises oxygen, and the mixture comprises acetic acid.

35. A method as defined in claim 5, wherein the intermediate oxidation product comprises adipic acid, the hydrocarbon comprises cyclohexane, the catalyst comprises a cobalt compound, the gaseous oxidant comprises oxygen, and the mixture comprises acetic acid.

36. A method as defined in claim 11, wherein the intermediate oxidation product comprises adipic acid, the hydrocarbon comprises cyclohexane, the catalyst comprises a cobalt compound, the gaseous oxidant comprises oxygen, and the mixture comprises acetic acid.

37. A method as defined in claim 14, wherein the intermediate oxidation product comprises adipic acid, the hydrocarbon comprises cyclohexane, the catalyst comprises a cobalt compound, the gaseous oxidant comprises oxygen, and the mixture comprises acetic acid.

38. A method as defined in claim 19, wherein the intermediate oxidation product comprises adipic acid, the hydrocarbon comprises cyclohexane, the catalyst comprises a cobalt compound, the gaseous oxidant comprises oxygen, and the mixture comprises acetic acid.

39. A method as defined in claim 21, wherein the intermediate oxidation product comprises adipic acid, the hydrocarbon comprises cyclohexane, the catalyst comprises a cobalt compound, the gaseous oxidant comprises oxygen, and the mixture comprises acetic acid.

40. A method as defined in claim 25, wherein the intermediate oxidation product comprises adipic acid, the hydrocarbon comprises cyclohexane, the catalyst comprises a cobalt compound, the gaseous oxidant comprises oxygen, and the mixture comprises acetic acid.

41. A method as defined in claim 29, wherein the intermediate oxidation product comprises adipic acid, the hydrocarbon comprises cyclohexane, the catalyst comprises a cobalt compound, the gaseous oxidant comprises oxygen, and the mixture comprises acetic acid.

42. A method as defined in claim 1, wherein
the intermediate oxidation product comprises a compound selected from a group consisting of adipic acid, phthalic acid, isophthalic acid, and terephthalic acid, and
the method further comprises a step of reacting said intermediate oxidation product with a third reactant selected from a group consisting of a polyol, a polyamine, and a polyamide in a manner to form a polymer of a polyester, or a polyamide, or a (polyimide and/or polyamideimide), respectively.

43. A method as defined in claim 42, further comprising a step of spinning the polymer into fibers.

44. A method as defined in claim 3, wherein
the intermediate oxidation product comprises a compound selected from a group consisting of adipic acid, phthalic acid, isophthalic acid, and terephthalic acid, and
the method further comprises a step of reacting said intermediate oxidation product with a third reactant selected from a group consisting of a polyol, a polyamine, and a polyamide in a manner to form a polymer of a polyester, or a polyamide, or a (polyimide and/or polyamideimide), respectively.

45. A method as defined in claim 44, further comprising a step of spinning the polymer into fibers.

46. A method as defined in claim 4, wherein
the intermediate oxidation product comprises a compound selected from a group consisting of adipic acid, phthalic acid, isophthalic acid, and terephthalic acid, and
the method further comprises a step of reacting said intermediate oxidation product with a third reactant selected from a group consisting of a polyol, a polyamine, and a polyamide in a manner to form a polymer of a polyester, or a polyamide, or a (polyimide and/or polyamideimide), respectively.

47. A method as defined in claim 46, further comprising a step of spinning the polymer into fibers.

48. A method as defined in claim 11, wherein
the intermediate oxidation product comprises a compound selected from a group consisting of adipic acid, phthalic acid, isophthalic acid, and terephthalic acid, and
the method further comprises a step of reacting said intermediate oxidation product with a third reactant selected from a group consisting of a polyol, a polyamine, and a polyamide in a manner to form a polymer of a polyester, or a polyamide, or a (polyimide and/or polyamideimide), respectively.

49. A method as defined in claim 48, further comprising a step of spinning the polymer into fibers.

50. A method as defined in claim 14, wherein
the intermediate oxidation product comprises a compound selected from a group consisting of adipic acid, phthalic acid, isophthalic acid, and terephthalic acid, and the method further comprises a step of reacting said intermediate oxidation product with a third reactant selected from a group consisting of a polyol, a polyamine, and a polyamide in a manner to form a polymer of a polyester, or a polyamide, or a (polyimide and/or polyamideimide), respectively.

51. A method as defined in claim 50, further comprising a step of spinning the polymer into fibers.

52. A method as defined in claim 21, wherein the intermediate oxidation product comprises a compound selected from a group consisting of adipic acid, phthalic acid, isophthalic acid, and terephthalic acid, and the method further comprises a step of reacting said intermediate oxidation product with a third reactant selected from a group consisting of a polyol, a polyamine, and a polyamide in a manner to form a polymer of a polyester, or a polyamide, or a (polyimide and/or polyamideimide), respectively.

53. A method as defined in claim 52, further comprising a step of spinning the polymer into fibers.

54. A method as defined in claim 25, wherein the intermediate oxidation product comprises a compound selected from a group consisting of adipic acid, phthalic acid, isophthalic acid, and terephthalic acid, and the method further comprises a step of reacting said intermediate oxidation product with a third reactant selected from a group consisting of a polyol, a polyamine, and a polyamide in a manner to form a polymer of a polyester, or a polyamide, or a (polyimide and/or polyamideimide), respectively.

55. A method as defined in claim 54, further comprising a step of spinning the polymer into fibers.

* * * * *